(12) United States Patent
Hammond et al.

(10) Patent No.: US 11,229,709 B2
(45) Date of Patent: Jan. 25, 2022

(54) DENDRIMER DRUG CONJUGATES FOR SUSTAINED INTRA-ARTICULAR DELIVERY

(71) Applicant: Massachusetts Institute of Technology, Cambridge, MA (US)

(72) Inventors: Paula T. Hammond, Newton, MA (US); Brett C. Geiger, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 20 days.

(21) Appl. No.: 16/625,955

(22) PCT Filed: Jun. 27, 2018

(86) PCT No.: PCT/US2018/039753
§ 371 (c)(1),
(2) Date: Dec. 23, 2019

(87) PCT Pub. No.: WO2019/005966
PCT Pub. Date: Jan. 3, 2019

(65) Prior Publication Data
US 2020/0155692 A1   May 21, 2020

Related U.S. Application Data

(60) Provisional application No. 62/526,618, filed on Jun. 29, 2017.

(51) Int. Cl.
*A61K 47/59* (2017.01)
*A61K 47/64* (2017.01)
*C08G 83/00* (2006.01)

(52) U.S. Cl.
CPC .......... *A61K 47/595* (2017.08); *A61K 47/593* (2017.08); *A61K 47/641* (2017.08); *C08G 83/003* (2013.01)

(58) Field of Classification Search
None
See application file for complete search history.

(56) References Cited

U.S. PATENT DOCUMENTS

| | | | |
|---|---|---|---|
| 8,658,148 B2 | 2/2014 | Avila et al. | |
| 9,017,644 B2 | 4/2015 | Baker, Jr. et al. | |
| 9,526,794 B2 | 12/2016 | Rangaramanujam et al. | |
| 9,610,250 B2 | 4/2017 | Fahmy et al. | |
| 9,611,357 B2 | 4/2017 | Avila et al. | |
| 2013/0004427 A1* | 1/2013 | El-Sayed | A61K 47/58 424/9.3 |
| 2014/0019508 A1 | 1/2014 | Sato | |

FOREIGN PATENT DOCUMENTS

| | | |
|---|---|---|
| WO | WO-2015/038493 A1 | 3/2015 |
| WO | WO-2017/074993 A1 | 5/2017 |
| WO | WO-2019/005966 A1 | 1/2019 |

OTHER PUBLICATIONS

Geiger et al., "Cartilage Penetrating Nanocarriers Enhance Drug Delivery and Efficacy in Osteoarthritis," MIT Koch Institute, Cambridge, MA.
Geiger et al., "Cartilage Penetrating Nanocarriers Formulation Improves Pharmacokinetics and Efficacy of Growth Factor in a Rat Surgical Model of Osteoarthritis," MIT Departments of Biological Engineering, Cambridge, MA.
Geiger et al., "Designing Drug Delivery Systems for Articular Joints," CEP Magazine (2018).
Geiger et al., Abstract for the Orthopaedic Research Society Annual Meeting, Mar. 10-13, 2018, New Orleans, LA.
International Preliminary Report on Patentability for International Application No. PCT/US2018/039753 dated Dec. 31, 2019.
International Search Report and Written Opinion for International Application No. PCT/US2018/039753 dated Oct. 9, 3018.
Luong et al., "PEGylated PAMAM dendrimers: Enhancing efficacy and mitigating toxicity for effective anticancer drug and gene delivery," Acta Biomaterialia, 43(12):14-29 (2016).
Qi et al., "Folate Receptor-Targeted Dendrimer-Methotrexate Conjugate for Inflammatory Arthritis," J Biomed Nanotechnol, 11(8):1431-1441 (2015).
Zhu et al., "PEGylated PAMAM Dendrimer-Doxorubicin Conjugates: In Vitro Evaluation and In Vivo Tumor Accumulation," Pharmaceutical Research, 27(1):161-174 (2009).

\* cited by examiner

*Primary Examiner* — Robert A Wax
*Assistant Examiner* — Randeep Singh
(74) *Attorney, Agent, or Firm* — Foley Hoag LLP; Alexander Akhiezer; Lawrence P. Tardibono

(57) ABSTRACT

A conjugated cationic dendrimer comprising end groups conjugated to charge-shielding groups, wherein some charge-shielding groups are chemically linked to active pharmaceutical ingredients.

30 Claims, 31 Drawing Sheets

Visual schematic of uptake experiment.

DENDRIMER DRUG CONJUGATES FOR SUSTAINED INTRA-ARTICULAR DELIVERY

RELATED APPLICATION(S)

This application is the U.S. National Stage of International Application No. PCT/US2018/039753, filed Jun. 27, 2018, which designates the U.S., published in English, and claims the benefit of U.S. Provisional Application No. 62/526,618, filed on Jun. 29, 2017. The entire teachings of the above application are incorporated herein by reference.

GOVERNMENT SUPPORT

This invention was made with Government support under Grant No. W81XWH-14-1-0544 awarded by the U.S. Army Medical Research and Material Command. The Government has certain rights in the invention.

BACKGROUND OF THE INVENTION

After traumatic joint injury, such as an ACL tear or military trauma, considerable inflammation in response to the injury leads to osteoarthritis in that joint 10-20 years after the injury in about 40-50% of cases. There is growing evidence to suggest that an interventional administration immediately following injury could delay or reverse this post-traumatic osteoarthritis. However, the existing drugs formulations are rapidly cleared from the joint space in hours, making them effectively useless as they cannot reach therapeutic doses in joint cartilage for therapeutically relevant amounts of time. Largely because of the drug delivery problem, no current therapy for post traumatic osteoarthritis exists.

SUMMARY OF THE INVENTION

It has now been discovered that the use of certain dendrimers conjugated to an active pharmaceutical ingredient (API) in an intraarticular injection provides for an extended delivery of such APIs to cartilage within articular joints, such as the knee, upon direct injection of the formulation into the joint. These certain dendrimers also enable penetration of cartilage tissue of approximately human thickness (~1 mm), which allows for even distribution of the drug to the entirety of the tissue.

In one example embodiment, the present application is a conjugated dendrimer, represented by the following structural formula:

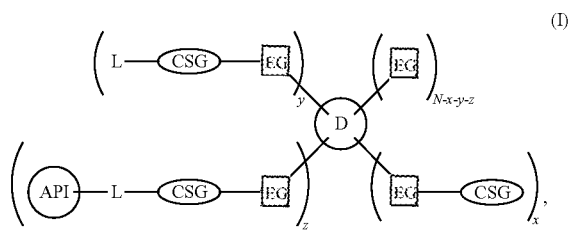

or a pharmaceutically acceptable salt thereof.

In structural formula (I), D is a cationic dendrimer having end groups EG, wherein each EG includes an amine moiety, each CSG is a charge-shielding group having molecular weight of less than or equal to 1085 Da; each L is a linker; each API is an active pharmaceutical ingredient; N is an integer power of 2 from 64 to 256; x, y, and z, each independently, is an integer from 1 to N; and the ratio of (x+y+z)/N is from about 0.1 to about 0.9.

Experiments described herein demonstrate that, unexpectedly, certain ranges of the percent functionalization of the dendrimer (ratio of (x+y+z)/N), the number of dendrimer branches (N), and the size of the charge-shielding groups (CSG) provides a clinically desirable combination of features, such as the dendrimer uptake by the tissue and biological activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
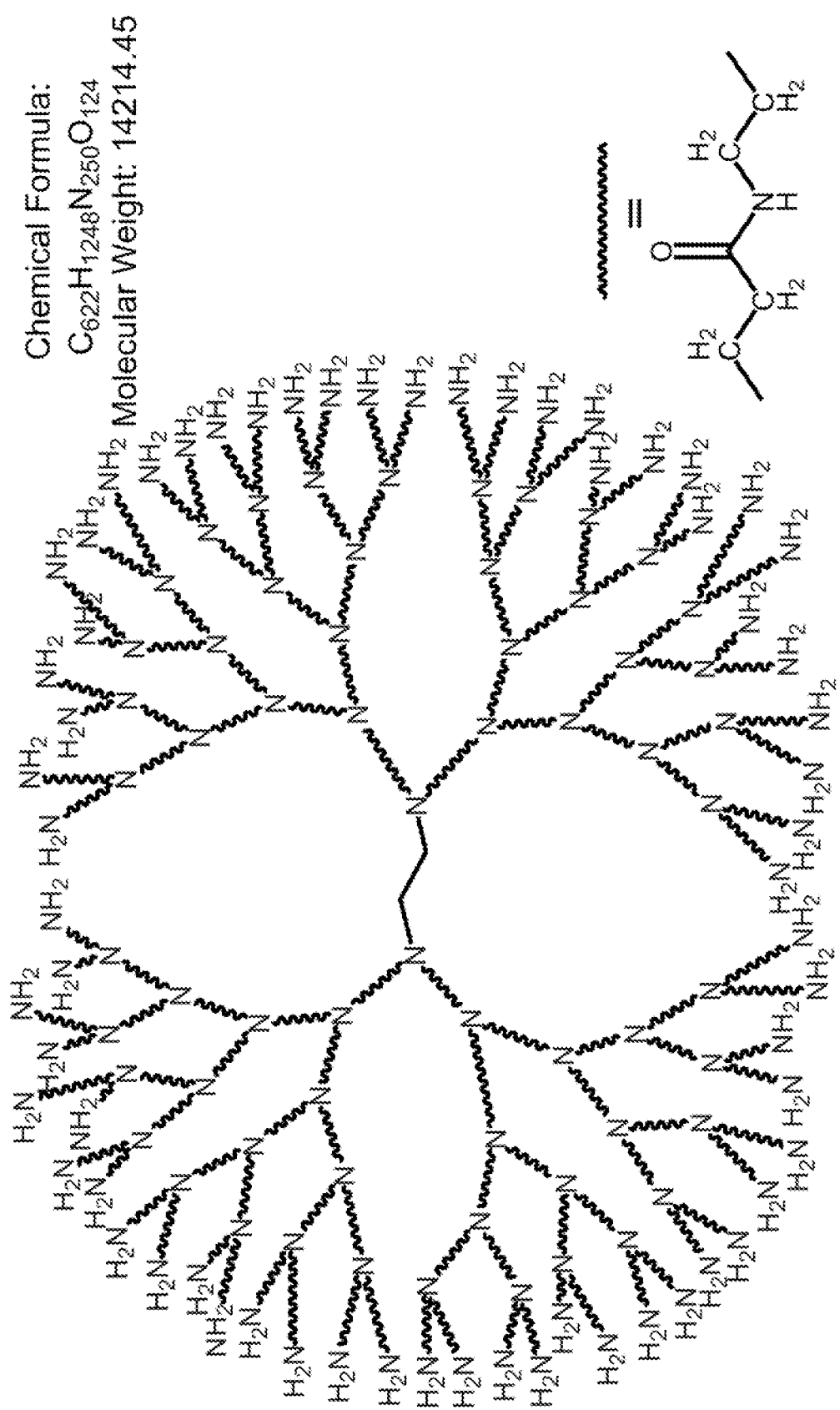
FIG. 1 is a representation of a chemical structure of a Generation 4 PAMAM dendrimer having the primary amines as end groups.

A description of example embodiments of the invention follows.

As used herein, the term "dendrimer" refers to repetitively branched oligomeric or polymeric molecules. A dendrimer is cationic if it is positively charged.

As used herein, "amino" include $-NH_2$, monoalkylamino and dialkylamino.

"Alkyl" means a saturated aliphatic branched or straight-chain monovalent hydrocarbon radical having the specified number of carbon atoms. Thus, "$(C_1-C_6)$ alkyl" means a radical having from 1-6 carbon atoms in a linear or branched arrangement. "$(C_1-C_6)$alkyl" includes methyl, ethyl, propyl, butyl, pentyl and hexyl.

As used herein, the term "amino acid" includes both a naturally occurring amino acid and a non-natural amino acid. The term "amino acid," unless otherwise indicated, includes both isolated amino acid molecules (i.e. molecules that include both, an amino-attached hydrogen and a carbonyl carbon-attached hydroxyl) and residues of amino acids (i.e. molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

"Naturally occurring amino acid" refers to any amino acid side chain moiety present in a natural amino acid.

A "peptide" is an oligomer of amino acids.

As used herein, the term "PEG" is interchangeable with polyethylene glycol and refers to a polether compound of general formula $-(OCH_2CH_2)_nO-$, where the terminal group can be H or any suitable substituent As used herein, a "poly(oxazoline)" refers to any of the general class of polymers obtained by polymerization of an oxazolone ring and having a repeat unit of the formula $-[N(C(O)R)-CH_2CH_2]-$, where R is a substituent on the carbonyl $-C(O)-$.

As used herein, a "polybetaine" is any polymer having a repeat unit derived from betaine, a crystalline, basic organic compound, (CH)NCHCOO.

As used herein, a "polyacrylate" refers to any polymer having a repeat unit $-[CH_2-C(C(O)O^-)]-$.

As used herein, a "polyacrylamide" refers to any polymer having a repeat unit $-[CH_2-CH(C(O)NH_2)]-$.

As used herein, a "fatty acid" refers to any a carboxylic acid consisting of a hydrocarbon chain and a terminal carboxyl group.

As used herein, a "phospholipid" refers to any molecule consisting of two hydrophobic fatty acid "tails" and a hydrophilic "head" consisting of a phosphate group.

As used herein, an "oligosaccharide" refers to any a carbohydrate whose molecules are composed of a relatively small number (typically 2-10) of monosaccharide (simple sugar) units. A "polysaccharide" is a chain of monosaccharides longer than 10 units.

As used herein, a "glycosaminoglycan" refer to any unbranched polysaccharide consisting of a repeating disaccharide unit, wherein the repeat unit includes an amino sugar (e.g. N-acetylglucosamine) and a uronic sugar (i.e. a carboxylic acid derivative of a sugar, such as glucuronic acid).

As used herein, a "polyanhydride" refers to any polymer having a repeat unit of structural formula $-[C(O)-R-C(O)O]-$, wherein R is a suitable carboxylic acid chain.

As used herein, a "polyglycidol" refers to any polymer that results from polymerization of glycidol, an oxirane of the structural formula:

optionally, with other repeat units.

As used herein, a "polyacetal" is any of a class of polymers that result from a condensation of aldehydes, such as, for example, polyoxymethylene (polyformaldehyde).

As used herein, a "polyglycerol" is any polymer having a structural formula where moiety R is any suitable carboxylic acid residue.

As used herein, a "polyphosphoester" is a polymer having a repeat unit of the following structural formula:

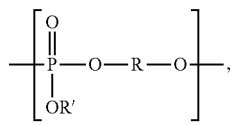

where R and R' are each a suitable alcohol residue.

As used herein, an "alcohol" refers to an organic compound having at least one C—OH moiety.

As used herein, an "arthritis" means "inflammation of a joint." In some forms of arthritis, such as osteoarthritis, the inflammation arises because the smooth covering (articular cartilage) on the ends of bones become damaged or worn. Osteoarthritis is usually found in one, usually weightbearing, joint. In some forms of osteoarthritis, such as post-traumatic osteoarthritis, the articular cartilage has become damaged or worn as a result of a traumatic joint injury.

As used herein, the term "about", when referring to a numerical value of a variable, means that the numerical value has a range of ±10%, for example ±5%, of the recited numerical value.

In a first example embodiments, the present invention is a conjugated dendrimer, represented by the following structural formula:

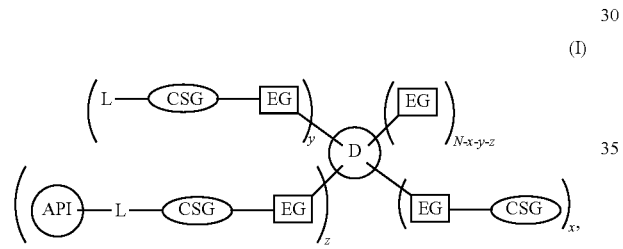

or a pharmaceutically acceptable salt thereof. In structural formula (I), D is a cationic dendrimer; EG is an end group of the cationic dendrimer D, and includes an amine moiety; each CSG is a charge-shielding group having a molecular weight of less than or equal to 5000 Da, for example from 2000 Da to 5000 Da; each L is a linker; each API is an active pharmaceutical ingredient; N is an integer power of 2 from 8 to 512, for example from 8 to 256; x, y, and z, each independently, is an integer from 1 to N; and the ratio of (x+y+z)/N is from about 0.2 to about 0.6. Dendrimers are described in terms of their Generation, G, or Gen, are defined as the number of repetitive polymer growth steps that is related to the value of variable N in structural formula (I) by a power law. For example, for PAMAM dendrimers, $N=2^{(Generation+2)}$, so that a Generation 6 PAMAM dendrimer, for example, possesses a number of end groups $N=2^8=256$.

In a first aspect of the first example embodiment, the API in structural formula (I) is an analgesic therapeutic agent or an osteoarthritis therapeutic agent selected from an anabolic growth factor (IGF-1, BMP-2, FGF-2, FGF-18, PDGF-BB, TGF-β); a non-steroidal anti-inflammatory therapeutic agent (Ibuprofen, diclofenac, Naproxen, a Cox 2 inhibitor (Celecoxib™); a corticosteroid (Dexamethasone, triamcinolone, betamethasone, methylprednisolone, cortisone); an antibody or an antibody fragment (specificity against TNF-α, IL1, NGF, VEGF or specificities against proteolytic enzymes such as ADAMTS 4 or 5, MMP 13, Cathepsin B, K); a proteolytic enzyme inhibitor (an inhibitors of ADAMTS 4 or 5, MMP 1,2,3,8,13,14, Cathepsin B,D,K cytokine inhibitors); an inhibitor of Interleukin 1 converting enzyme (ICE), or inhibitors of IL-1α and IL-1β, IL-6, IL-8, TNF-α, TGF-β; a tissue inhibitors of metalloprotases (TIMPs); a receptor antagonist or anti-inflammatory cytokines (a I-1-receptor antagonist, IL-4, IL-10). The values and example values of the remainder of the variables in structural formula (I) are as defined above and below with respect to various aspects of the first example embodiments.

In a second aspect of the first example embodiment, the cationic dendrimer is selected from a polyamidoamine (PAMAM), a polypropylenimine (PPI), a triazine dendrimer, a polyetherimine (PETIM), a poly(L-Lysine) dendrimer, and a poly(ester) dendrimer. The repeat units of these polymers are depicted below:

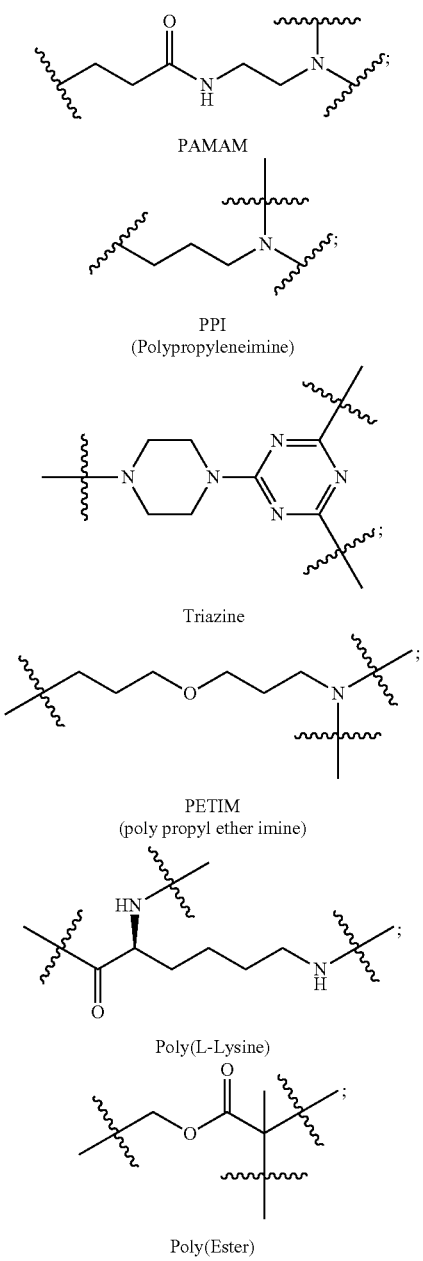

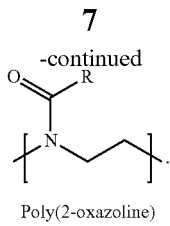

Poly(2-oxazoline)

The values and example values of the remainder of the variables in structural formula (I) are as defined above and below with respect to various aspects of the first example embodiments.

In a third aspect of the first example embodiment, the charge-shielding group is selected from a polyethylene glycol (PEG) (for example, $PEG_{2-100}$), a poly(2-oxazoline), a polybetaine (carboxybetaine, sulfobetaine, phosphobetaine), a polyacrylate, a polyacrylamide, an amino acid (either natural or unnatural); a peptide, such as poly(hydroxyethyl l-glutamine) or poly(hydroxyethyl-1-asparagine) (PHEA), or a peptide of a sequence WYRGRL, GFOGER, or RGD; a fatty acid or phospholipid, an oligosaccharide such as dextran, cyclodextrin, chistosan, heparin, chondroitin, keratin, or other naturally occurring sugars; a glycosaminoglycan, such as a hyaluronate, chondroitin sulfate, keratin sulfate, or heparan sulfate; an polyanhydride, a polyglycidol; a polyacetal; a poly-glycerol, and a polyphosphoester. The values and example values of the remainder of the variables in structural formula (I) are as defined above and below with respect to various aspects of the first example embodiments.

In a fourth aspect of the first example embodiment, the linker is selected from any one of the chemical moieties depicted or described below:

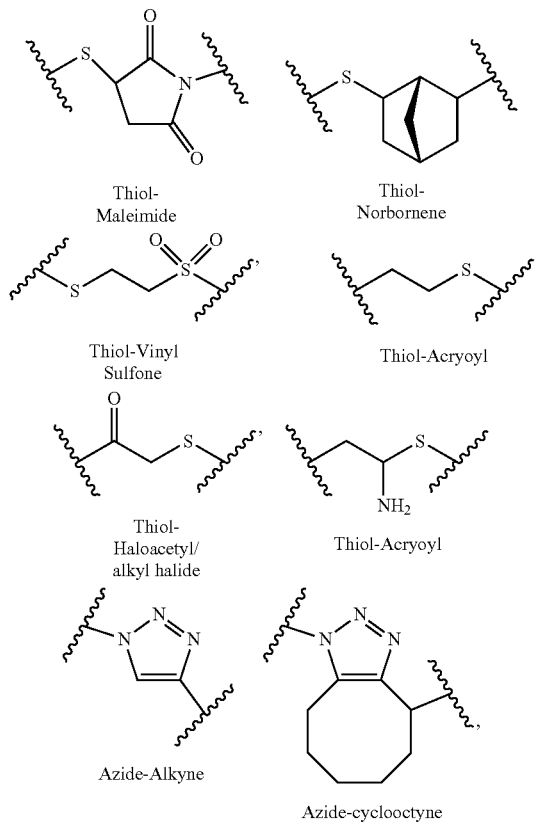

a moiety represented by the following structural formula

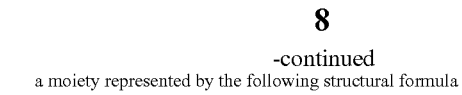

which results from a chemical coupling of a cysteine residue with a moiety represented by the structural formula

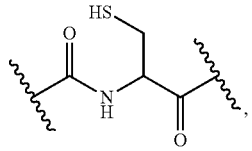

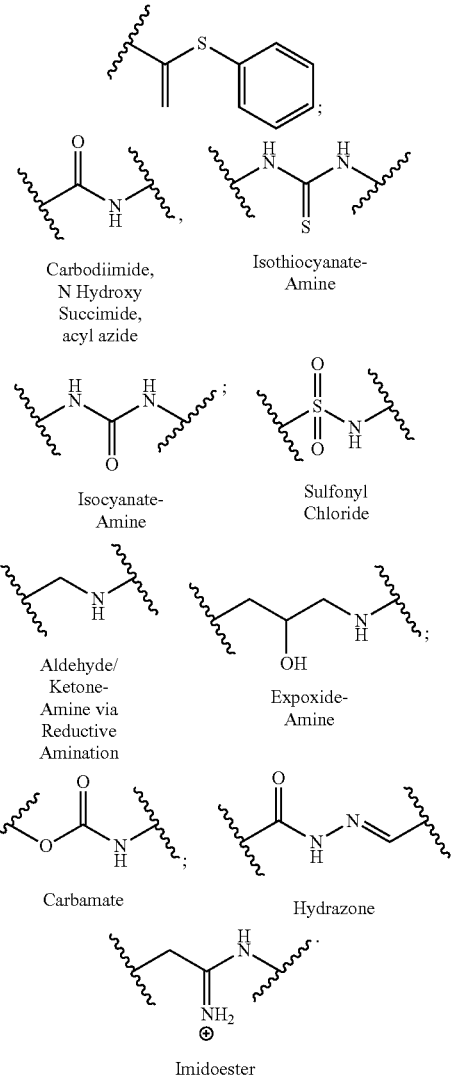

The values and example values of the remainder of the variables in structural formula (I) are as defined above and below with respect to various aspects of the first example embodiments.

In a fifth aspect of the first example embodiment, the linker contains a peptide substrate of any one or more of the following enzymes: matrix metalloprotease 13 (MMP13) (for example, a peptide containing at least one of sequences TSED-LVVQ, TVKP-VFEV, TVKP-IFGV (Aggrecan), or GPPGPQG-LAGQ (collagen 3/4)); Cathepsin B (for example, a peptide containing the sequence NFFG-VGGE); Cathepsin K (for example, a peptide containing at least one of sequences GKPG-KSGE (Collagen II) or AGAR-GSDG); ADAMTS-4 (for example, peptide containing a sequence VDIPEN-FFGVGG); and ADAMTS-5 (for example, a peptide containing a sequence NITEGE-ARGSVI). The values and example values of the remainder of the variables in structural formula (I) are as defined above and below with respect to various aspects of the first example embodiments.

In a sixth aspect of the first example embodiment, the API is selected from a biologically active polypeptide, a monoclonal antibody, a nonsteroidal anti-inflammatory drug (NSAIDS), a matrix metallopeptidase inhibitor, a cytokine inhibitor, and a nucleic acid. The values and example values of the remainder of the variables in structural formula (I) are as defined above and below with respect to various aspects of the first example embodiments.

In a seventh aspect of the first example embodiment, each linker L includes a thiol-maleimide moiety represented by the following structural formula:

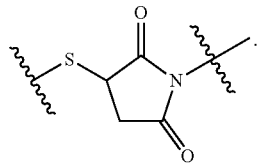 [SMILES: *SC1CC(=O)N(*)C1=O]

The values and example values of the remainder of the variables in structural formula (I) are as defined above and below with respect to various aspects of the first example embodiments.

In an eight aspect of the first example embodiment, the API is selected from Insulin-like Growth Factor 1 (IGF-1,) a Fibroblast Growth Factor 18 (FGF-18), dexamethasone, a matrix metallopeptidase MMP13 inhibitor, an IL1 receptor antagonist, a TGFB inhibitor, a TNFalpha inhibitor, and kartogenin. The values and example values of the remainder of the variables in structural formula (I) are as defined above and below with respect to various aspects of the first example embodiments.

In a ninth aspect of the first example embodiment, the cationic dendrimer D is a PAMAM, and each end-group EG is —$NH_2$. The values and example values of the remainder of the variables in structural formula (I) are as defined above and below with respect to various aspects of the first example embodiments.

In a tenth aspect of the first example embodiment, each charge-shielding group CSG is a polyethylene glycol (PEG) having from 2 to 100 repeat units. The values and example values of the remainder of the variables in structural formula (I) are as defined above and below with respect to various aspects of the first example embodiments.

In an eleventh aspect of the first example embodiment, the API is a biologically active polypeptide. The values and example values of the remainder of the variables in structural formula (I) are as defined above and below with respect to various aspects of the first example embodiments.

In a twelfth aspect of the first example embodiment, the cationic dendrimer is a G4 PAMAM having, wherein each end-group is —$NH_2$ and N is 64 or a G6 PAMAM, wherein each end-group is —$NH_2$ and N is 256. The values and example values of the remainder of the variables in structural formula (I) are as defined above and below with respect to various aspects of the first example embodiments.

In a thirteenth aspect of the first example embodiment, each charge-shielding group CSG is a PEG having from 8 to 12 units. The values and example values of the remainder of the variables in structural formula (I) are as defined above and below with respect to various aspects of the first example embodiments.

In a fourteenth aspect of the first example embodiment, each linker L is a thiol-maleimide moiety represented by the following structural formula:

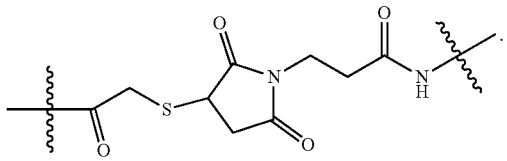 [SMILES: *NC(=O)CCN1C(=O)CC(SCC(*)=O)C1=O]

The values and example values of the remainder of the variables in structural formula (I) are as defined above and below with respect to various aspects of the first example embodiments.

In a fifteenth aspect of the first example embodiment, each API is a human IGF-1 (P05019). The values and example values of the remainder of the variables in structural formula (I) are as defined above and below with respect to various aspects of the first example embodiments.

In a sixteenth aspect of the first example embodiment, the conjugated dendrimer is represented by the following structural formula:

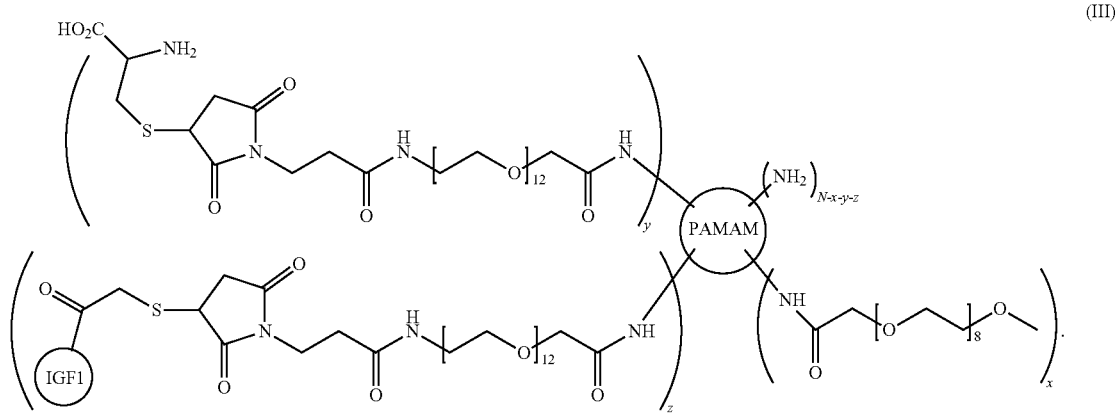

(III)

The values and example values of the remainder of the variables in structural formula (I) are as defined above and below with respect to various aspects of the first example embodiments.

In a seventeenth aspect of the first example embodiment, N is 64 and the ratio of (x+y+z)/N is from about 0.3 to about 0.5. The values and example values of the remainder of the variables in structural formula (I) are as defined above and below with respect to various aspects of the first example embodiments.

In an eighteenth aspect of the first example embodiment, N is 256 and the ratio of (x+y+z)/N is from about 0.4 to about 0.6. The values and example values of the remainder of the variables in structural formula (I) are as defined above and below with respect to various aspects of the first example embodiments.

In a second example embodiment, the present invention is a pharmaceutical composition, comprising a conjugated dendrimer of any one or more aspects one through eighteen of the first example embodiment, in a pharmaceutically acceptable carrier.

In a third example embodiment, the present invention is a method of treating a disorder of an articular joint cartilage. The method comprises administering to a subject in need thereof a therapeutically effective amount of a conjugated dendrimer of any one or more aspects of the first example embodiment or a pharmaceutical composition of the second example embodiment. In a first aspect of the third example embodiment, the disorder is an articular joint arthritis or an articular joint cartilage injury. In a second aspect of the third example embodiment, the administering is by intra-articular injection.

In a fourth example embodiment, the present invention is a conjugated dendrimer, represented by structural formula (I),

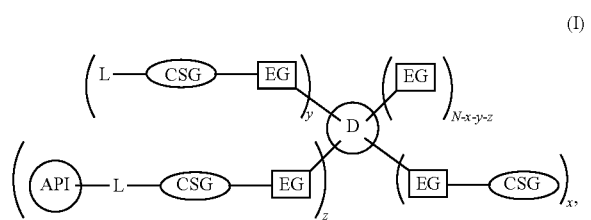

(I)

or a pharmaceutically acceptable salt thereof. In the 4$^{th}$ example embodiment, D is a cationic dendrimer having end groups EG, wherein each EG includes an amine moiety, each CSG is a charge-shielding group having molecular weight of less than or equal to 1085 Da; each L is a linker; each API is an active pharmaceutical ingredient; N is an integer power of 2 from 64 to 256; x, y, and z, each independently, is an integer from 1 to N; and the ratio of (x+y+z)/N is from about 0.1 to about 0.9.

In a first aspect of the 4$^{th}$ example embodiment, each CSG is a charge-shielding group having molecular weight of equal to or greater than 200 and less than 400 Da; N is 64; and the ratio of (x+y+z)/N is from about 0.6 to about 0.9. For example, the ratio can be 0.75 to 0.85. The remainder of the values and example values in structural formula (I) are as described above and below with respect to various aspects of the 4$^{th}$ example embodiment.

In a second aspect of the 4$^{th}$ example embodiment, each charge-shielding group CSG is a PEG having from 8 to 12 units; N is 64; and the ratio of (x+y+z)/N is from about 0.2 to about 0.6. For example, the ratio can be 0.3 to 0.45. The remainder of the values and example values in structural formula (I) are as described above and below with respect to various aspects of the 4$^{th}$ example embodiment.

In a third aspect of the 4$^{th}$ example embodiment, each CSG is a charge-shielding group having molecular weight of equal to or greater than 400 and less than 614 Da; N is 64; and the ratio of (x+y+z)/N is from about 0.2 to about 0.6. For example, the ratio can be 0.3 to 0.45. The remainder of the values and example values in structural formula (I) are as described above and below with respect to various aspects of the 4$^{th}$ example embodiment.

In a fourth aspect of the 4$^{th}$ example embodiment, each CSG is a charge-shielding group having molecular weight of equal to or greater than 614 and less than 820 Da; N is 64; and the ratio of (x+y+z)/N is from about 0.15 to about 0.50. For example, the ratio can be 0.25 to 0.4. The remainder of the values and example values in structural formula (I) are as described above and below with respect to various aspects of the 4$^{th}$ example embodiment.

In a fifth aspect of the 4$^{th}$ example embodiment, each CSG is a charge-shielding group having molecular weight of equal to or greater than 820 and less than or equal to 1085 Da; N is 64; and the ratio of (x+y+z)/N is from about 0.1 to about 0.4. For example, the ratio can be 0.2 to 0.35. The remainder of the values and example values in structural formula (I) are as described above and below with respect to various aspects of the 4$^{th}$ example embodiment.

In a sixth aspect of the 4$^{th}$ example embodiment, each CSG is a charge-shielding group having molecular weight of equal to or greater than 200 and less than 400 Da; N is 256; and the ratio of (x+y+z)/N is from about 0.4 to about 0.8. For example, the ratio can be 0.7 to 0.8. The remainder of the values and example values in structural formula (I) are as described above and below with respect to various aspects of the 4$^{th}$ example embodiment.

In a seventh aspect of the 4th example embodiment, each charge-shielding group CSG is a PEG having from 8 to 12 units; N is 256; and the ratio of (x+y+z)/N is from about 0.2 to about 0.6. For example, the ratio can be 0.3 to 0.5. In another example, the ratio can be 0.4 to 0.5. The remainder of the values and example values in structural formula (I) are as described above and below with respect to various aspects of the 4$^{th}$ example embodiment.

In an eighth aspect of the 4$^{th}$ example embodiment, each CSG is a charge-shielding group having molecular weight of equal to or greater than 400 and less than 614 Da; N is 256; and the ratio of (x+y+z)/N is from about 0.2 to about 0.6. For example, the ratio can be 0.3 to 0.5. The remainder of the values and example values in structural formula (I) are as described above and below with respect to various aspects of the 4$^{th}$ example embodiment.

In a ninth aspect of the 4$^{th}$ example embodiment, each CSG is a charge-shielding group having molecular weight of equal to or greater than 614 and less than 820 Da; N is 256; and the ratio of (x+y+z)/N is from about 0.15 to about 0.5. For example, the ratio can be 0.2 to 0.4. The remainder of the values and example values in structural formula (I) are as described above and below with respect to various aspects of the 4$^{th}$ example embodiment.

In a tenth aspect of the 4$^{th}$ example embodiment, each CSG is a charge-shielding group having molecular weight of equal to or greater than 825 and less than or equal to 1085 Da; N is 256; and the ratio of (x+y+z)/N is from about 0.15 to about 0.4. For example, the ratio can be 0.3 to 0.4. The remainder of the values and example values in structural formula (I) are as described above and below with respect to various aspects of the 4th example embodiment.

In an eleventh aspect of the fourth example embodiment, the cationic dendrimer includes at least one repeat units represented by the following structural formulas:

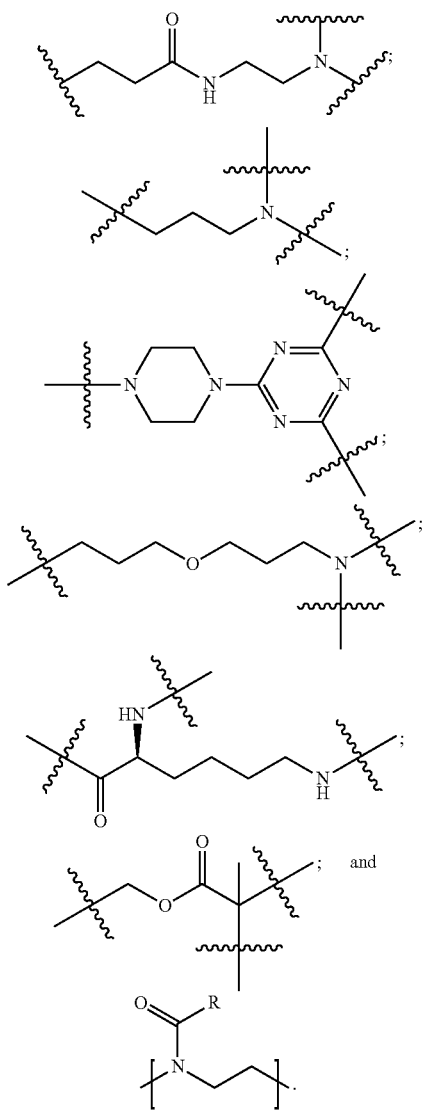

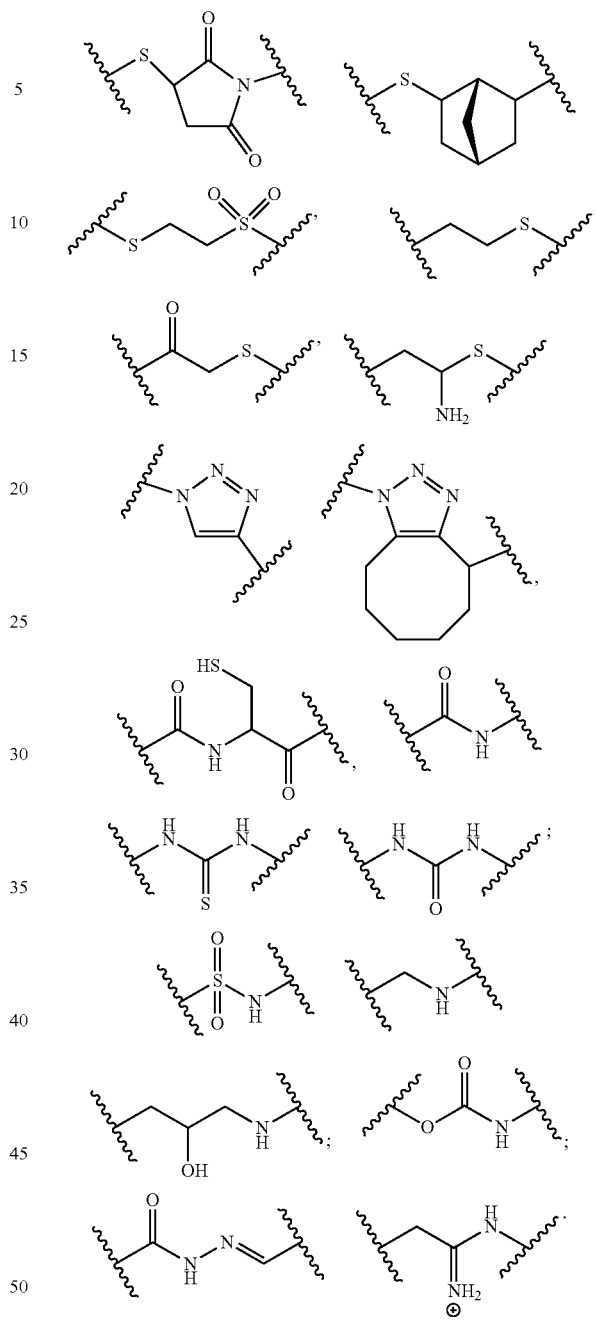

The remainder of the values and example values of structural formula (I) of the 4th example embodiments are as described with respect to the first to tenth aspects thereof.

In a twelfth aspect of the fourth example embodiment, the charge-shielding group is selected from a polyethylene glycol (PEG), a poly(2-oxazoline), a polybetaine, a polyacrylate, a polyacrylamide, an amino acid; a peptide; a fatty acid or phospholipid, an oligosaccharide; a glycosaminoglycan; a polyanhydride, a polyglycidol; a polyacetal; a polyglycerol, and a polyphosphoester. For example, the charge shielding groups can be a polyethylene glycol (PEG). The remainder of the values and example values of structural formula (I) of the 4th example embodiments are as described with respect to the first to eleventh aspects thereof.

In a 13th aspect of the fourth example embodiment, the linker is represented by any one of the following structural formulas:

The remainder of the values and example values of structural formula (I) of the 4th example embodiments are as described with respect to the first to twelfth aspects thereof.

In a 14th aspect of the fourth example embodiment, the linker includes a moiety represented by any one of the following structural formulas:

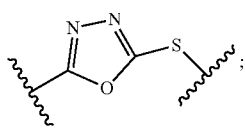

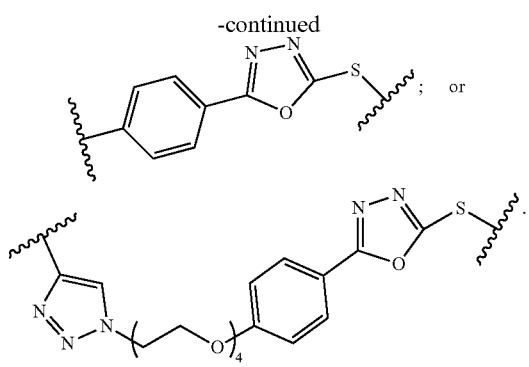
; or

The remainder of the values and example values of structural formula (I) of the 4th example embodiments are as described with respect to the first to twelfth aspects thereof.

In a 15th aspect of the fourth example embodiment, the linker include a peptide substrate of any one or more of the following enzymes: matrix metalloprotease 13 (MMP13); Cathepsin B; Cathepsin K; ADAMTS-4; and ADAMTS-5.

The remainder of the values and example values of structural formula (I) of the 4th example embodiments are as described with respect to the first to 14th aspects thereof.

In a 16th aspect of the fourth example embodiment, the API is selected from a biologically active polypeptide, a monoclonal antibody, a nonsteroidal anti-inflammatory drug (NSAIDS), a matrix metallopeptidase inhibitor, a cytokine inhibitor, and a nucleic acid.

The remainder of the values and example values of structural formula (I) of the 4th example embodiments are as described with respect to the first to 15th aspects thereof.

In a 17th aspect of the fourth example embodiment, the API is selected from Insulin-like Growth Factor 1 (IGF-1,) a Fibroblast Growth Factor 18 (FGF-18), dexamethasone, a matrix metallopeptidase MMP13 inhibitor, an IL1 receptor antagonist, a TGFB inhibitor, a TNFalpha inhibitor, and kartogenin.

The remainder of the values and example values of structural formula (I) of the 4th example embodiments are as described with respect to the first to 15th aspects thereof.

In an 18th aspect of the fourth example embodiment, the cationic dendrimer D is a PAMAM, and each end-group EG is —NH$_2$.

The remainder of the values and example values of structural formula (I) of the 4th example embodiments are as described with respect to the first to 17th aspects thereof.

In a 19th aspect of the fourth example embodiment, each linker L includes a thiol-maleimide moiety represented by the following structural formula:

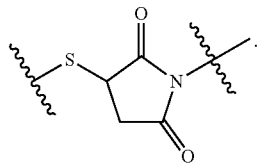 [SMILES: *SC1CC(=O)N(*)C1=O]

The remainder of the values and example values of structural formula (I) of the 4th example embodiments are as described with respect to the first to 18th aspects thereof.

In an 20th aspect of the fourth example embodiment, the cationic dendrimer is a G4 PAMAM, wherein each end-group is —NH$_2$ and N is 64 or a G6 PAMAM, wherein each end-group is —NH$_2$ and N is 256.

The remainder of the values and example values of structural formula (I) of the 4th example embodiments are as described with respect to the first to 19th aspects thereof.

In a 21st aspect of the fourth example embodiment, each linker L is a thiol-maleimide moiety represented by the following structural formula:

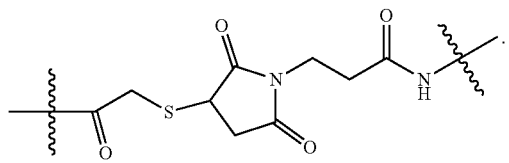 [SMILES: *NC(=O)CCN1C(=O)CC(SCC(*)=O)C1=O]

The remainder of the values and example values of structural formula (I) of the 4th example embodiments are as described with respect to the first to 20th aspects thereof.

In a 22nd aspect of the fourth example embodiment, each API is a human IGF-1.

The remainder of the values and example values of structural formula (I) of the 4th example embodiments are as described with respect to the first to 21st aspects thereof.

In a 23rd aspect of the fourth example embodiment, the conjugated dendrimer is represented by the following structural formula (III)

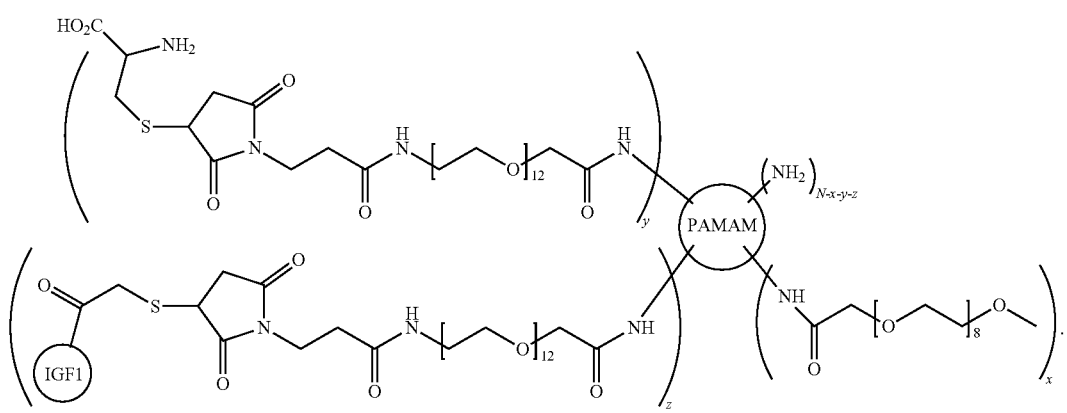

Values and preferred values of the variables in structural formula (III) are defined above with respect to the $1^{st}$ to $23^{rd}$ aspects of the fourth example embodiment.

In a fifth example embodiment, the present invention is a pharmaceutical composition, comprising a conjugated dendrimer of any one of the aspects of the fourth example embodiments described herein.

In a sixth example embodiment, the present invention is a method of treating a disorder of an articular joint cartilage, comprising administering by an intra-articulate injection to a subject in need thereof a therapeutically effective amount of a conjugated dendrimer of any one of the aspects of the fourth example embodiment described herein or a pharmaceutical composition according to the fifth example embodiment. In various aspects of the sixth example embodiment, the disorder is an articular joint arthritis or an articular joint cartilage injury.

EXEMPLIFICATION

In an example embodiment, the conjugated dendrimer described herein is an amine terminated polyamidoamine (PAMAM) dendrimer that has been conjugated at its end groups with a number of poly ethylene glycol (PEG) polymer chains. The PAMAM dendrimer is depicted shown in FIG. 1 and FIG. 2.

Figure 2:
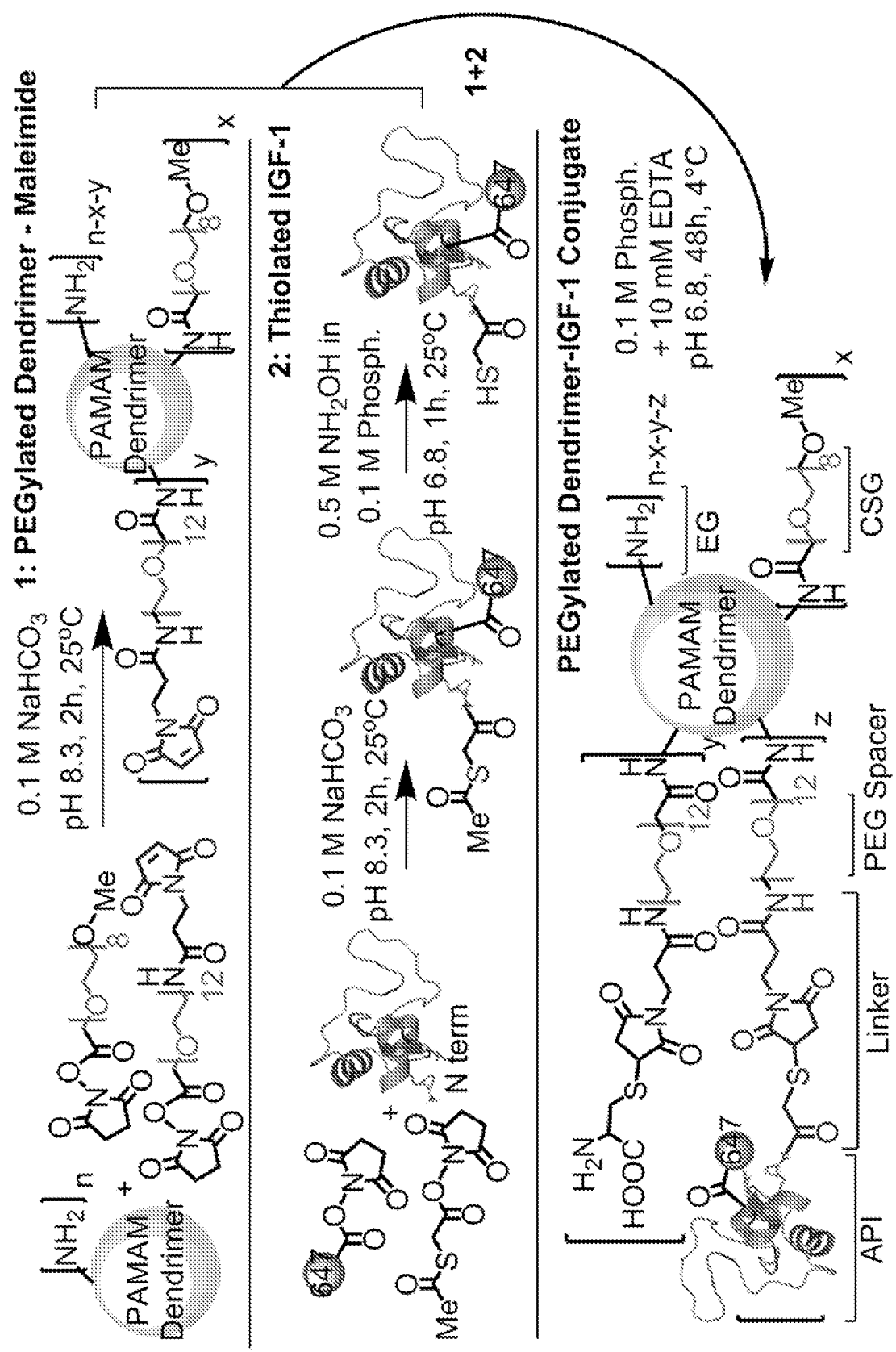
FIG. 2 is schematic diagram of an example conjugated dendrimer of the present invention.

In the embodiment shown in FIG. 1 and FIG. 2, the core PAMAM dendrimer is 5 nm in diameter, 14200 Da, and has 64 terminal amines for a generation 4 molecule. A generation 6 molecule is 7 nm in diameter, 50000-58000 Da, and has 210-256 terminal amines. The dense surface charge provided by these amines makes the dendrimers extremely effective in partitioning into negatively charged cartilage tissue but can be toxic. Experiments described herein have shown that chemically reacting about 40% of these amines with short, 8-unit long, PEG polymer molecules can make the dendrimer-PEG molecule nontoxic to cartilage cells and tissue while retaining a high degree of uptake/partitioning into cartilage tissue. This is the key to sustained release and cartilage penetration.

Example 1: Conjugation of an API to a PAMAM Dendrimer

Conjugation of an API of interest in osteoarthritis, insulin like growth factor 1 (IGF 1), involved first reacting a longer PEG (12 units, "PEG spacer" in FIG. 2) with the dendrimer core. This PEG (SM(PEG)-12) also had a reactive maleimide group at its distal end. In a separate mixture, the native IGF 1 protein was reacted with a N-succinimidyl S-acetylthioacetate (SATA) that converts an amine group on the protein to a protected thiol. After the thiol is deprotected, mixing the dendrimer-PEG-maleimide with the IGF 1-thiol under certain conditions causes a specific reaction between the maleimide and thiol. This links together the dendrimer and IGF 1 in a permanent fashion ("Linker" in FIG. 2). The reaction conjugates additional maleimide groups to the dendrimer—these reactive groups are quenched by addition of the thiol containing amino acid cysteine. FIG. 2 shows a schematic of the final dendrimer-drug conjugate in its current form.

Synthesis of Partially PEGylated Dendrimers

PEGylated dendrimers were synthesized by reacting the terminal primary amine groups of PAMAM dendrimers (Sigma) of Generation 4 (MW: 14.2 kDa, 64 terminal amines) or Generation 6 (MW: 50-58 kDa, 210-256 terminal amines) with NHS-mPEG (PEG, MW: 550, Creative PEG-Works) of approximately 8 repeat units and NHS-mPEG-maleimide (PEG-mal, MW: 866, Thermo-Fisher) of approximately 12 repeat units. Molar ratios were defined as a percentage of PAMAM terminal amines (for example, G4-PEG-40% indicates a molar ratio of PEG:PAMAM of approximately 0.40*64=25). Of the total mol PEG added to each mol dendrimer, 5 mol were PEG-mal for G4 dendrimers and 10 mol were PEG-mal for G6 dendrimers. The total mol of PEG and PEG-mal were added to an aqueous solution of PAMAM in 0.1 M NaHCO$_3$ at pH ~8.0 and reacted for 2 h at room temperature with rotation. The reaction mixture was purified by ultracentrifugation (Amicon Ultra-4, Millipore) at 3000×g for 15 minutes, 3 times. The purified compound was characterized for % end-group PEGylation by $^1$H NMR by integral ratio and MALDI-TOF Synthesis of Partially PEGylated Dendrimer-Drug Conjugates Recombinant human IGF-1 (Biovision, UniProt #P05019) was dissolved at 1 mg/mL in 0.1 M NaHCO$_3$. N-Succinimidyl S-acetylthioacetate (SATA, Thermo-Fisher) dissolved in DMSO was added to the solution at a 2.5:1 molar ratio. After 10 minutes, Alexa Fluor 647 dissolved in DMSO was added to the solution at a 2:1 molar ratio. The mixture was allowed to react for an additional 2 hours at room temperature with rotation. The reaction was purified by desalting with a 5 kDa cutoff dextran column (Thermo-Fisher), using 0.1 M phosphate buffer adjusted to pH 6.8. Fractionation was based on absorbance at 280 and 650 nm. The fluorescent IGF-SATA was then deprotected with a 0.5 M hydroxylamine, 0.01 M EDTA solution in phosphate buffer at pH 8.0 until maximum thiol concentration was identified by Ellman's assay, about 50 minutes. The reaction was again purified by desalting on a dextran column with 0.01 M EDTA in phosphate buffer as the eluent. Finally, the fluorescent IGF-SH was reacted with 50 nmol maleimide functionalized PEGylated for 2-3 days at 4° C. in 0.1 M phosphate buffer, pH 6.8. The final product was purified by cationic exchange chromatography with a series of increasingly concentrated phosphate buffers, pH 6.8, used as the eluent.

Figure 6:
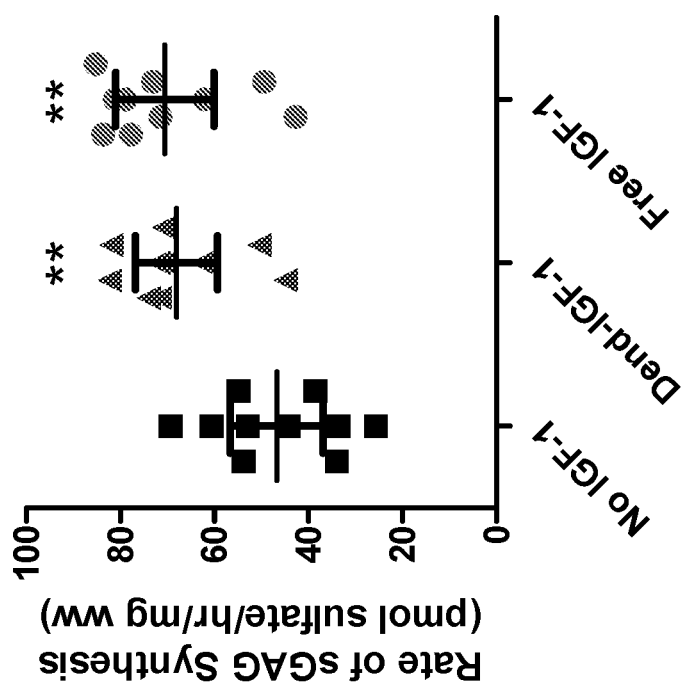
FIG. 6 is a scatter plot demonstrating enhanced synthesis of proteoglycans by cartilage tissue in response to the dendrimer-API conjugate of the present invention and unmodified API

IGF-1 bioactivity for cartilage sulfated proteoglycan synthesis was assessed by measuring radioactive $^{35}$S incorporation into ex vivo bovine cartilage over a period of 24-48 hours. Cartilage explant disks were obtained via biopsy punch from the femoropatellar grooves of young (1-2 week) bovine knee joints (Research 87, MA). The cylindrical explants of 3 mm were then placed into a machined template and trimmed to 1 mm depth with a razor blade. Disks were allowed to recover from the harvest process overnight in low glucose DMEM with additives of 1% Pen-Strep, L-Proline, ascorbic acid, HEPES, and nonessential amino acids. 5 μCi/mL 35S sulfate (Perkin-Elmer) was added to the media concurrently with treatment of dendrimer-IGF-1 or unmodified, free IGF-1 (0.5 μM IGF-1). After the incorporation period, tissue explants were washed in PBS, weighed, and digested with Proteinase K (Roche). Radiolabel incorporation was measured by liquid scintillation counting (Perkin-Elmer), normalized to tissue wet weight, and expressed as a function of time. FIG. 6 shows this normalized rate of sulfated proteoglycan synthesis in response to each treatment.

Bioactivity of the conjugates was assessed by observing proliferative activity in NIH 3T3 fibroblasts in response to treatment. Percent of cells in S Phase, as measured in flow-cytometric cell cycle analysis was used as a measure of proliferation. In each biological replicate, cells were thawed and seeded overnight in T-75 flasks in DMEM+10 v/v %

FBS+1 v/v % Pen-Strep. After overnight recovery from thawing, high serum media was replaced with 0.5 v/v % FBS containing media for 48 hours. Then, Dendrimer-IGF-1 or IGF-1 was added to a final concentration of 100 ng/mL for 24 hours. Cells were then incubated with 10 µM EdU for 2 hours, fixed and permeabilized. EdU was labeled using a Click-It-EdU kit (Alexa Fluor 488, Thermo-Fisher) and cells were stained with DAPI. Dual EdU-488/DAPI stained cells were analyzed by flow cytometry (FACS Celesta, BD) to 20,000 events per sample.

Figure 7:
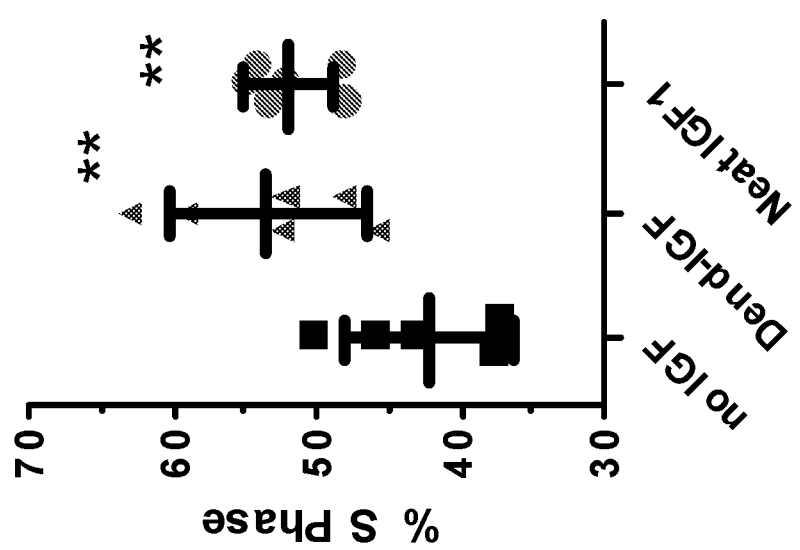
FIG. 7 shows a scatter plot demonstrating enhanced proliferation of NIH 3T3 cells in response to the dendrimer-API conjugate of the present invention and unmodified API

Data were gated for single cells and then for cell cycle phase based on EdU staining and DAPI staining. FIG. 7 shows a scatter plot representing percent of NIH 3T3 cells in S phase following 24 hours of treatment with no IGF-1, dendrimer-IGF-1, or free IGF-1, as determined by cell cycle flow cytometry with DAPI and EdU staining. Data are means+95% CI, N=6 biological replicates, statistics by one way ANOVA.

The data presented in FIGS. 6 and 7 shows that the API conjugated to the dendrimer depicted in FIG. 2 remains bioactive.

Example 2: Molecular Weight-Dependent PEGylation Ratio Window Ensures High Cell Viability/High API Uptake Combination Uptake Experiments Cartilage explant disks were obtained via biopsy punch from the femoropatellar grooves of young (1-2 week) bovine knee joints (Research 87, MA). The cylindrical explants of 3 or 6 mm were then placed into a machined template and trimmed to 1 mm depth with a razor blade. Disks were allowed to recover from the harvest process overnight in low glucose DMEM with additives of 10% FBS (v/v), 1% Pen-Strep, L-Proline, ascorbic acid, HEPES, and non-essential amino acids. Disks were then washed in PBS and incubated for 48 hours in 10 uM PEG-dendrimer-Alexa Fluor 647 in PBS at 37° C. in individual wells in a 96 well plate on a plate shaker. Disks were removed from the dendrimer bath and the bath was measured for fluorescence at 645/675 nm ex/em. Bath fluorescence measurements were converted to concentration of dendrimer using a calibration curve and subtracted from the total amount of fluorescent dendrimer added to determine % uptake of dendrimer into the cartilage.

Cell Viability Experiments

CHON-001 human chondrocytes (ATCC) were seeded into a 96 well plate overnight in DMEM+10% FBS (v/v)+1% Pen-Strep. PEG-dendrimers at varying % PEG and concentrations were added to the media and incubated at 37° C. and 5% $CO_2$ for 48 hours. Cell-Titer-Glo (Promega) reagent was added to each well, and ATP concentration measured via luminescence at 1 s integration time. % viability was recorded as luminescence as a fraction of that of untreated cells.

Figure 3A:
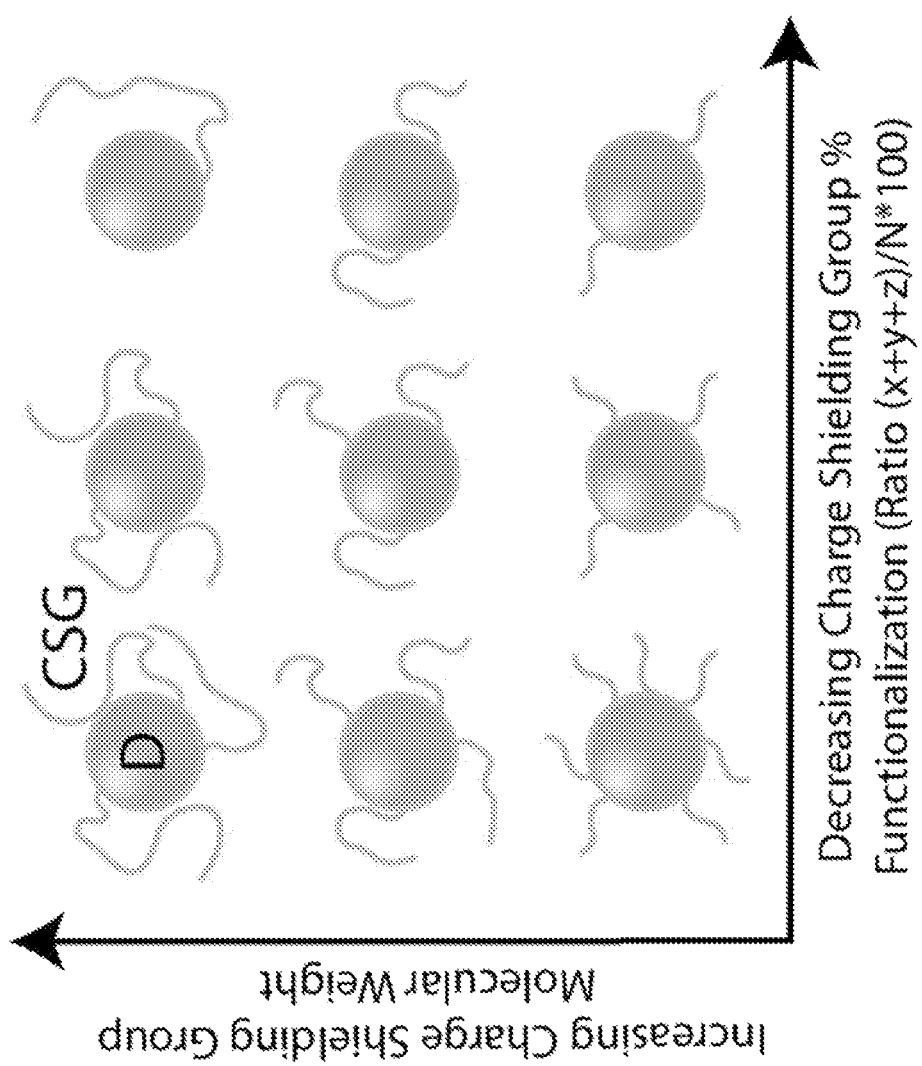
FIG. 3A illustrates a schematic diagram of the approach of generating a library of dendrimers with different molecular weights and end group ratios of charge shielding group
Figure 3B:
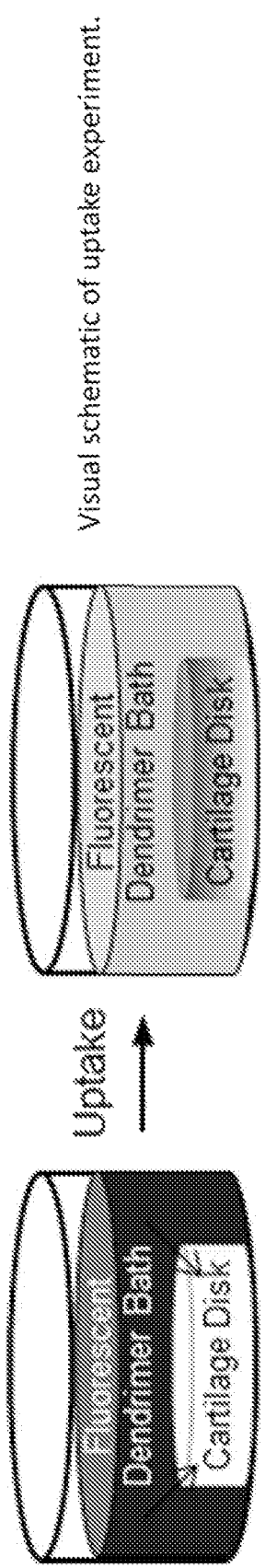
FIG. 3B is a schematic diagram of experiments to measure cartilage uptake of the library of dendrimers from FIG. 3A at different molecular weight of charge shielding group, end ratio of charge shielding group, and number of end groups N.

A schematic diagram depicting the various molecular weights and ratios (or % PEGylation) of PEG chosen for testing is shown in FIG. 3A The schematic diagram of the experimental set up is shown in FIG. 3B. The results of measurements of the dendrimer uptake are presented as plots shown in FIGS. 3C through 3K.

Uptake—Freshly harvested cow cartilage disks (3 mm×1 mm) were added to a 10 uM aqueous solution of each dendrimer-PEG formulation. After 48 hours, cartilage was removed, measured for fluorescence, and the % of that 10 uM dendrimer-PEG that bound to the tissue was measured as % uptake Viability—Human cartilage cells (from ATCC, CHON-001) were incubated with 10 uM of each dendrimer formulation for 48 hours—the % of cells alive after this experiment was measured as % viability.

A desirable formulation would have nearly 100% cell viability and as high of % uptake as possible. While at low extent of PEGylation, dendrimers have high uptake performance but kill far too many cells, too much PEG results in dendrimers having very low % uptake.

Figure 3C:
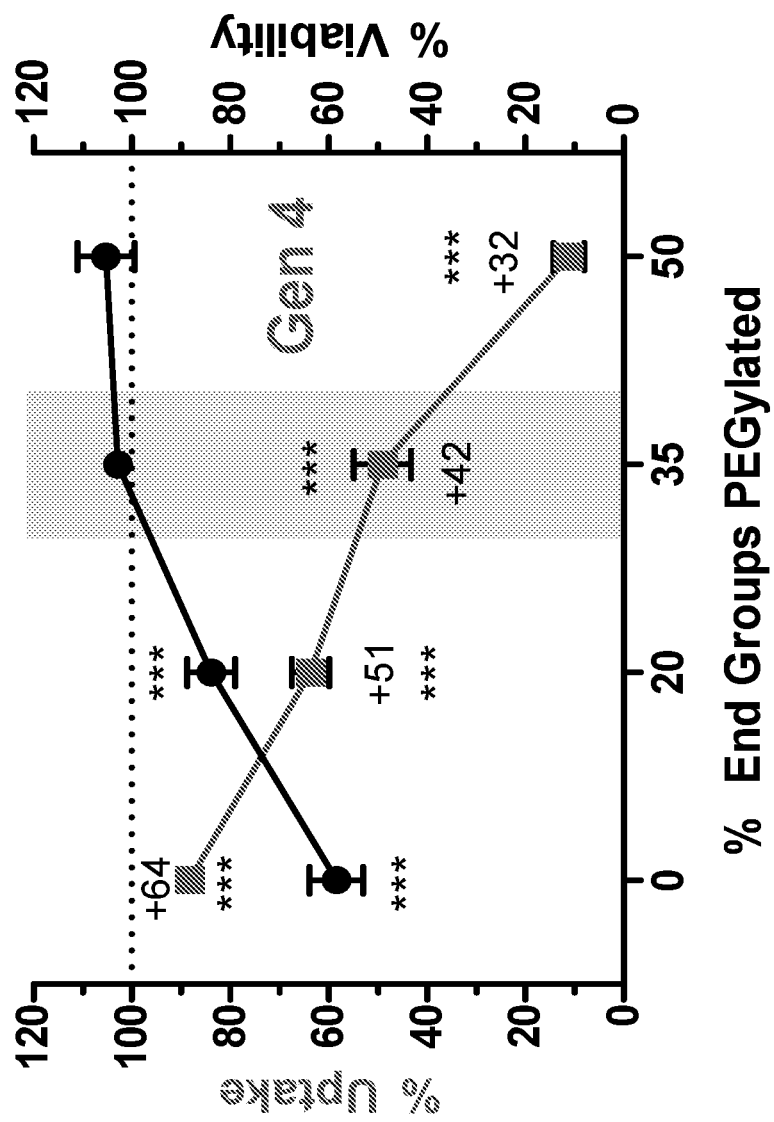
FIGS. 3C through 3K represent the plots showing dendrimer uptake and cell viability for Gen 4 and Gen 6 PAMAM of EG modification with various molecular weights and ratios of charge shielding group.
Figure 3D:
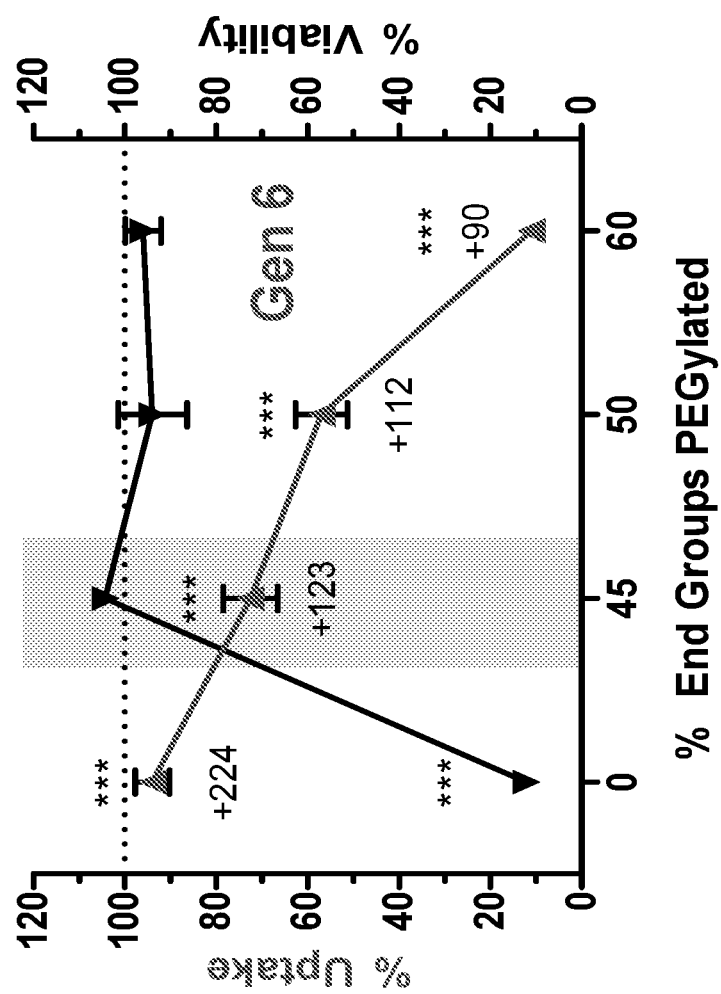

Analysis of the data presented in FIGS. 3C and 3D indicates that when the dendrimer is PAMAM Generation 4 or 6 (N=64 or 256) and the charge shielding group is $PEG_8$, the conjugated dendrimer has high uptake at all % PEGylation (ratio) between 20-60% (0.2-0.6), and there is little toxicity. Thus for N=64-256 (Generation 4-Generation 6), PEG MW of about 400-624 (PEG8-PEG12), a ratio of 0.20 to 0.60 (20-60%) is unexpectedly advantageous.

Further experiments investigated the dependency of the unexpectedly beneficial PEGylation window on the molecular weight of the PEG chain and generation of the dendrimer. FIG. 3A is a schematic representation of a library of the conjugated dendrimers used to test the effect of charge shielding group molecular weight and ratio on cartilage binding performance. FIG. 3C-K is a plot depicting the amount of conjugated dendrimer taken up into tissue (% total) as a function of PEGylation percentage (that corresponds to the ratio $(x+y+z)/N$, as described and claimed herein) alongside the cell viability of chondrocytes (% surviving cells) as a function of same. FIGS. 3C, 3E-G represent data collected for Gen 4 (N=64) PAMAM dendrimers with different molecular weights (shown as number of repeat units of PEG) and ratios of PEG. FIGS. 3D, 3H-K represent data collected for Gen 6 (N=256) PAMAM dendrimers with different molecular weights (shown as number of repeat units of PEG) and ratios of PEG.

The data presented in FIGS. 3C-3K demonstrate that there unexpectedly exists a dendrimer generation and PEG molecular weight (i.e. chain-length)-dependent target PEGylation window (corresponding to the ratio $(x+y+z)/N$) at which the combination of the uptake and cell survival are especially beneficial.

Figure 3E:
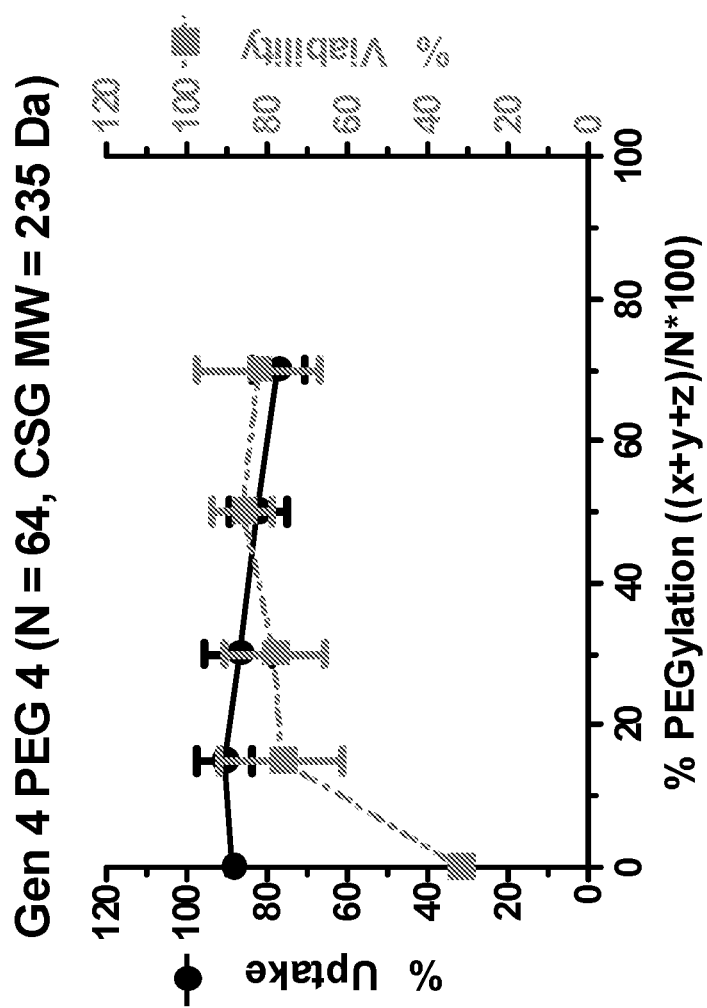

The data presented in FIG. 3E indicates that when the dendrimer is Generation 4 (N=64) and the charge shielding group is $PEG_4$, the conjugated dendrimer had high uptake at all % PEGylation (ratio $(x+y+z)/N$). However, unacceptable toxicity was observed at % PEGylation below 60%. Thus for N=64 (Generation 4), PEG MW of about 200-400 (PEG4-PEG7), a ratio of 0.6 to 0.9 (PEGylation 60-90%) is unexpectedly advantageous.

Figure 3F:
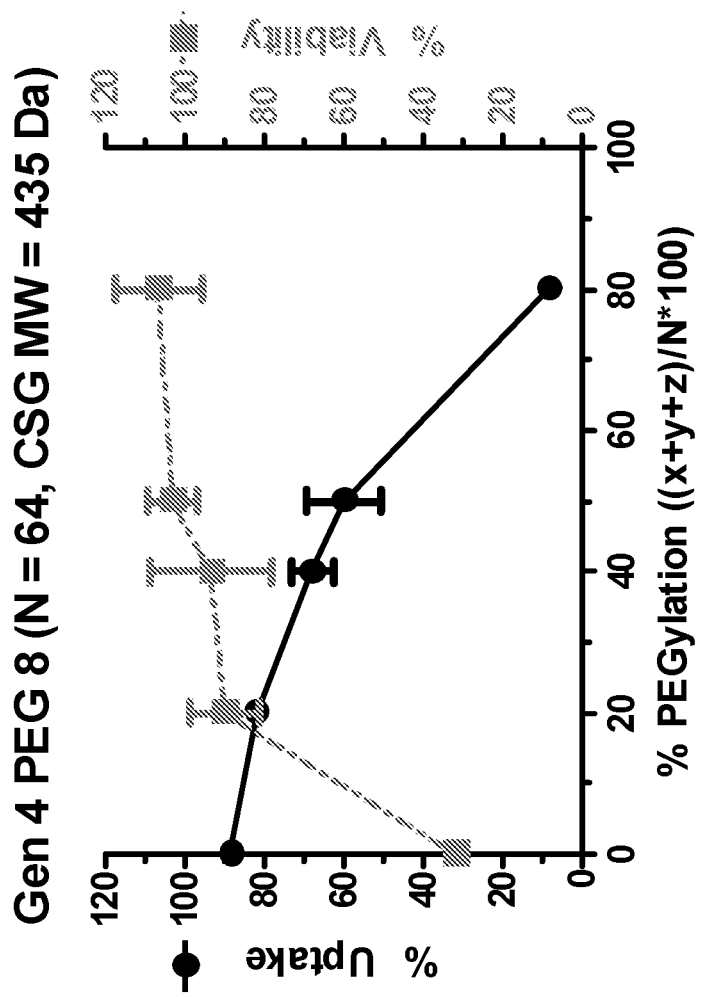

Analysis of the data presented in FIG. 3F indicates that when the dendrimer is Generation 4 (N=64) and the charge shielding group is $PEG_8$, the conjugated dendrimer has high uptake at all % PEGylation (ratio) between 20-60% (0.2-0.6), and there is little toxicity. Thus for N=64 (Generation 4), PEG MW of about 400-615 (PEG8-PEG12), a ratio of 0.20 to 0.60 (20-60%) is unexpectedly advantageous.

When the dendrimer is Generation 4 (N=64) and the charge shielding group is $PEG_{13}$, the conjugated dendrimer has high uptake at % PEGylation between 15-50%, and there is little toxicity. Thus, for N=64 (Generation 4), PEG MW of about 615-820 (PEG13-17), a ratio of 0.15 to 0.50 (15-50%) is unexpectedly advantageous.

Figure 3G:
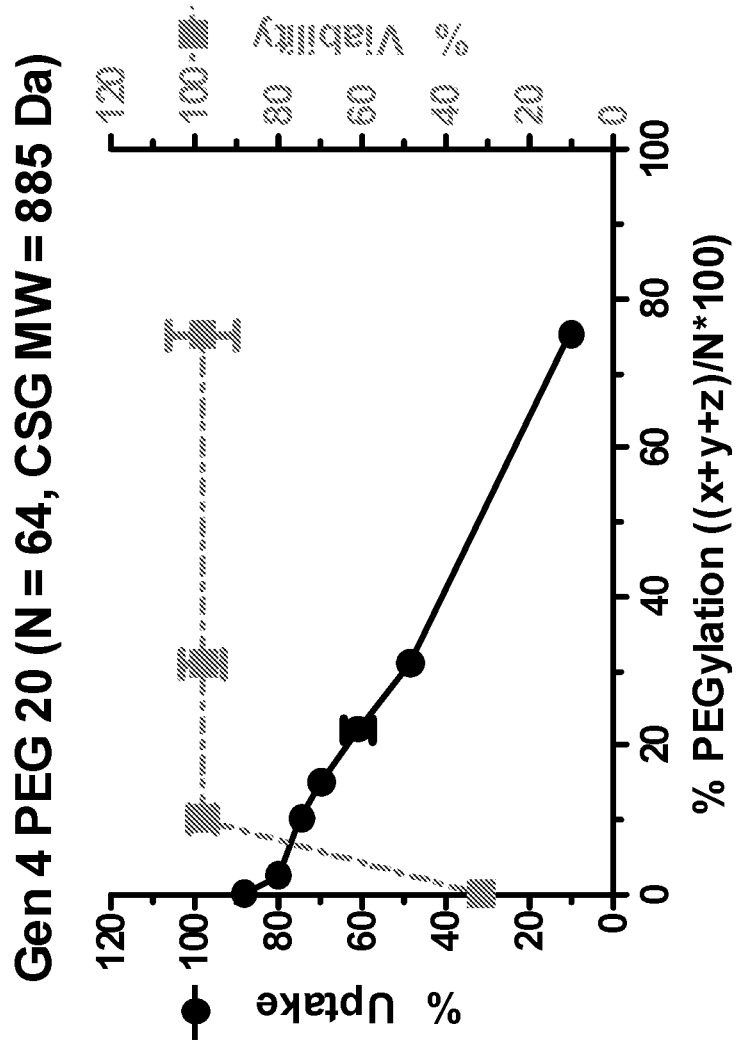

Analysis of the data presented in FIG. 3G indicates that when the dendrimer is Generation 4 (N=64) and charge shielding group is $PEG_{20}$, the conjugated dendrimer has high uptake at % PEGylation between 10-40%, and there is little toxicity. Thus, for N=64 (Generation 4), PEG MW of about 820-1085 (PEG17-PEG23), a ratio of 0.10 to 0.40 (10-40%) is unexpectedly advantageous.

Figure 3H:
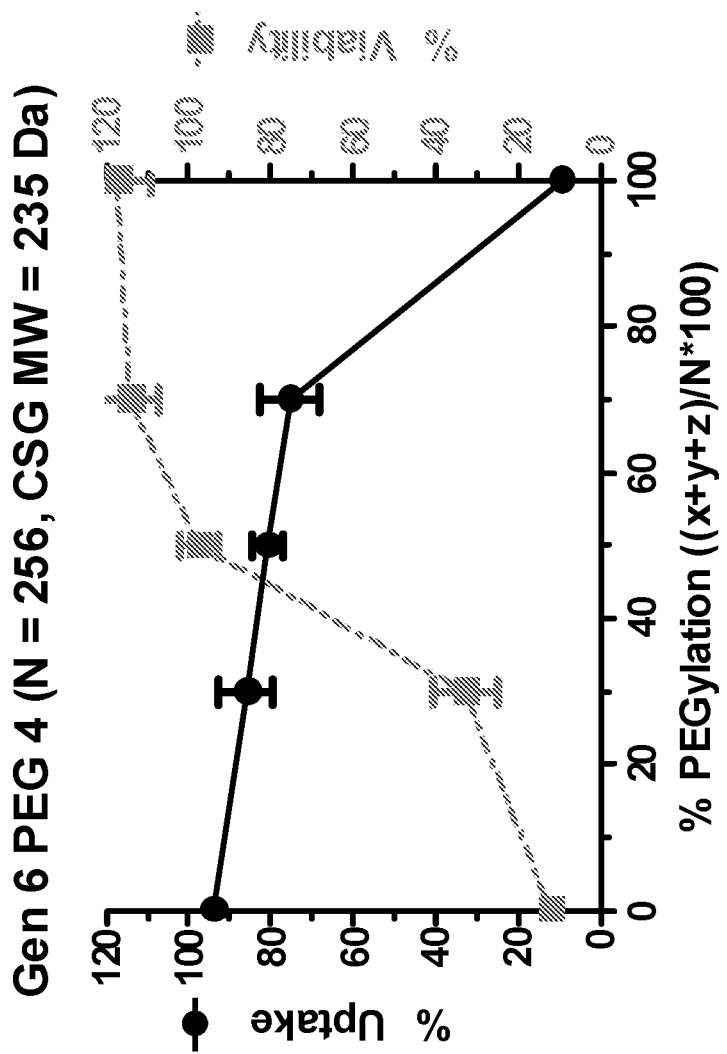

Analysis of the data presented in FIG. 3H indicates that when the dendrimer is Generation 6 (N=256) and the charge shielding group is PEG4, the conjugated dendrimer had high uptake at % PEGylation between 40 and 80% (ratio (x+y+z)/N), and there is little toxicity. Thus for N=256 (Generation 6), PEG MW of about 200-400 (PEG4-PEG7), a ratio of 0.4 to 0.8 (PEGylation 40-80%) is unexpectedly advantageous.

Figure 3I:
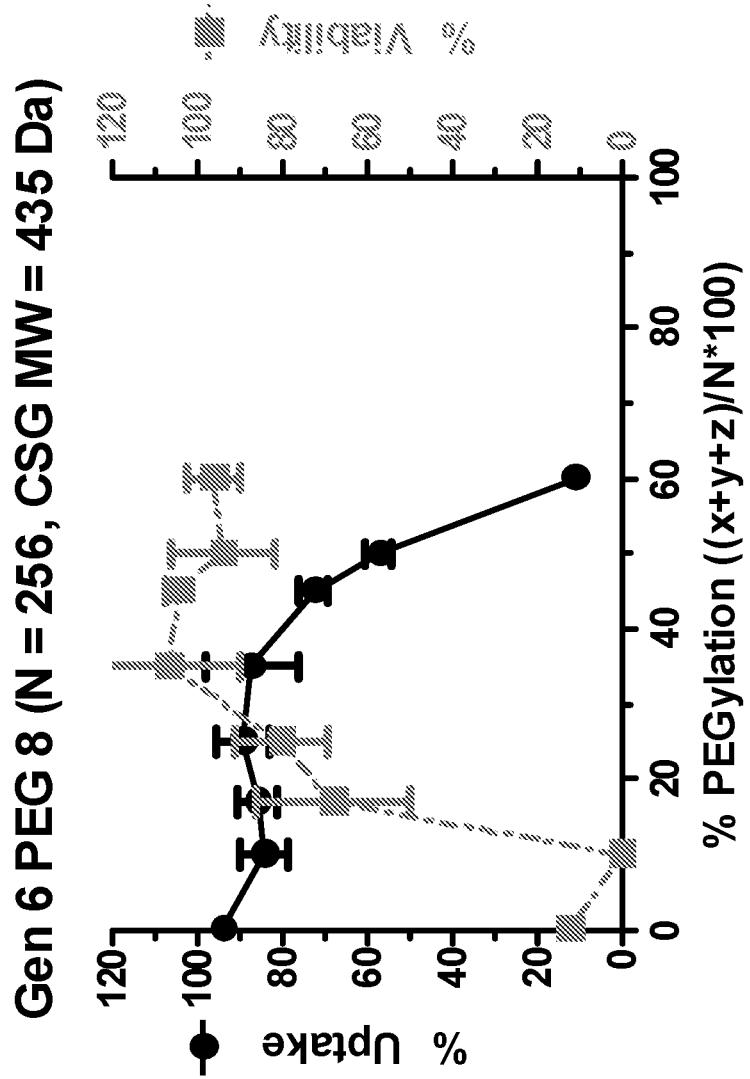

Analysis of the data presented in FIG. 3I indicates that when the dendrimer is Generation 6 (N=256) and the charge shielding group is $PEG_8$, the conjugated dendrimer has high uptake at % PEGylation (ratio) between 20-60% (0.2-0.6), and there is little toxicity. Thus for N=256 (Generation 6), PEG MW of about 400-615 (PEG8-PEG12), a ratio of 0.20 to 0.60 (20-60%) is unexpectedly advantageous.

Figure 3J:
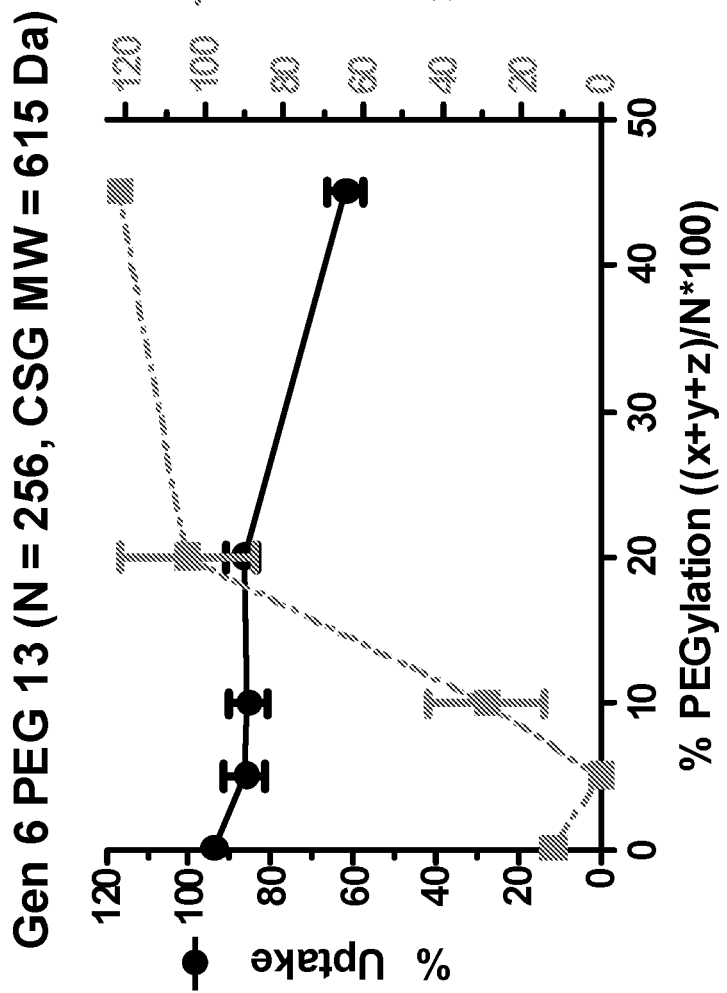

Analysis of the data presented in FIG. 3J indicates that when the dendrimer is Generation 6 (N=256) and the charge shielding group is $PEG_{13}$, the conjugated dendrimer has high uptake at % PEGylation between 15-50%, and there is little toxicity. Thus, for N=256 (Generation 6), PEG MW of about 615-820 (PEG13-17), a ratio of 0.15 to 0.50 (15-50%) is unexpectedly advantageous.

Figure 3K:
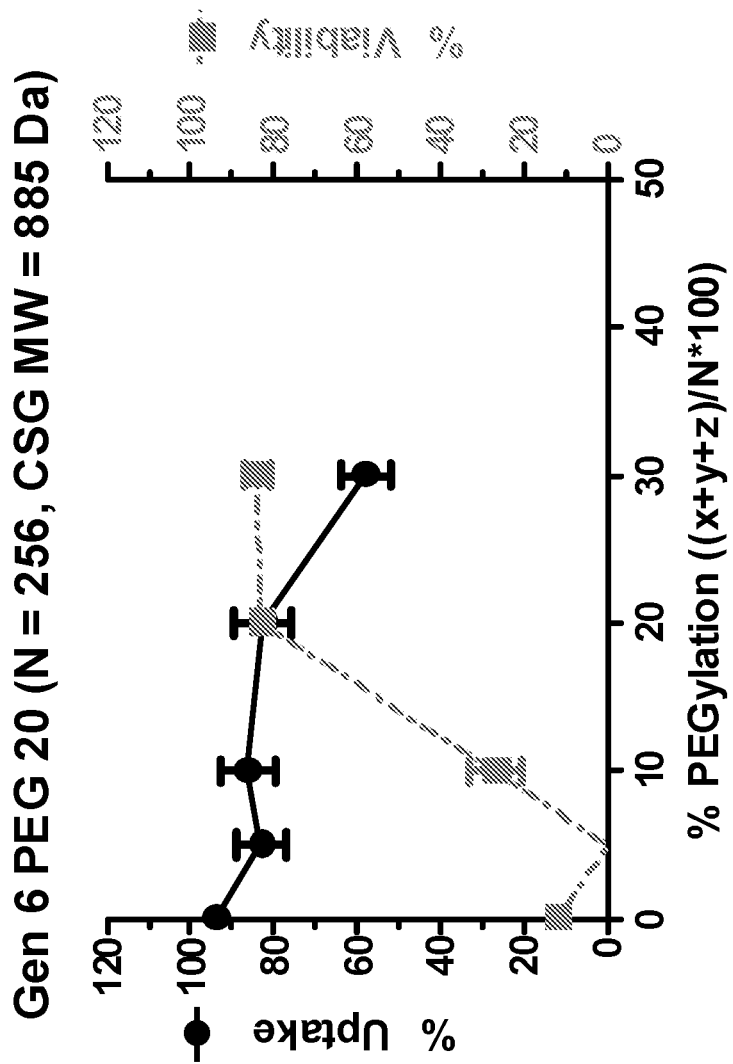

Analysis of the data presented in FIG. 3K indicates that when the dendrimer is Generation 6 (N=256) and charge shielding group is $PEG_{20}$, the conjugated dendrimer has high uptake at % PEGylation between 15-40%, and there is little toxicity. Thus, for N=256 (Generation 6), PEG MW of about 820-1085 (PEG17-PEG23), a ratio of 0.15 to 0.40 (15-40%) is unexpectedly advantageous.

Example 3: Biodistribution and Half-Life of Conjugated Dendrimers

PEGylated Dendrimer-drug conjugates greatly extend drug residence time in rat joints.

Sprague-Dawley rats (Taconic) of 12 weeks of age were put under anesthesia and injected intra-articularly with Gen 4 35% PEG-IGF-1 conjugate (D=PAMAM, Generation=4, N=64, Ratio (x+y+z)/N=0.35, CSG=$PEG_8$, CSG MW=435 Da, API=IGF-1) or Gen 6 45% PEG-IGF-1 conjugate (D=PAMAM, Generation=6, N=256, Ratio (x+y+z)/N=0.45, CSG=$PEG_8$, CSG MW=435 Da, API=IGF-1) in both knees to a final knee joint concentration of approximately 10 uM dendrimer. Prior to injection, knee joints were shaved and disinfected with iodine scrub and 70% ethanol, 3 times. Rats were serially imaged at timepoints using a IVIS Spectrum (Perkin-Elmer) instrument at 640/680 nm. Images were quantified by drawing an anatomical Region of Interest (ROI) around the knee joint, applying to each image, and measuring radiant efficiency within the ROI on Living Image (Perkin-Elmer) software. Data for each treatment group was fit to a single exponential decay curve (FIG. 4C) with a terminal plateau assigned to all groups based on imaging an untreated rat. This fit curve was used to generate a joint residence time half-life (FIG. 4D) for each formulation, which was used with relevant concentrations (dose injected and drug $EC_{50}$) to calculate an effective time at therapeutic dose in the joint.

The results are presented in FIGS. 4A, 4B, 4C, and 4D.

Figure 4A:
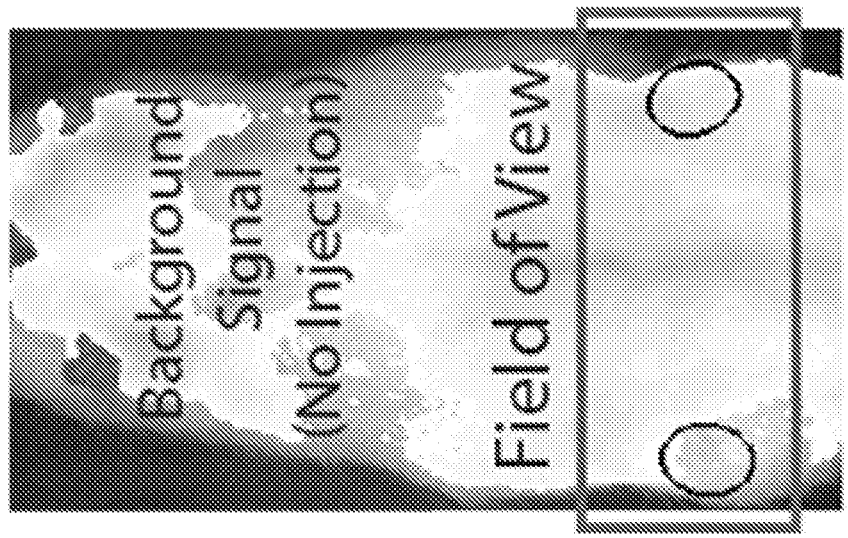
FIGS. 4A and 4B are photographs of rat knee joints post intra-articular injection of the conjugated dendrimers of the present invention, fluorescently marked.

As shown in FIG. 4A, rats were injected intra-articularly (directly into their knee joints) with fluorescent IGF-1 alone or IGF-1 conjugated to Gen 4 35% PEG-IGF-1 or Gen 6 45% PEG-IGF-1 dendrimer formulations.

Figure 4B:
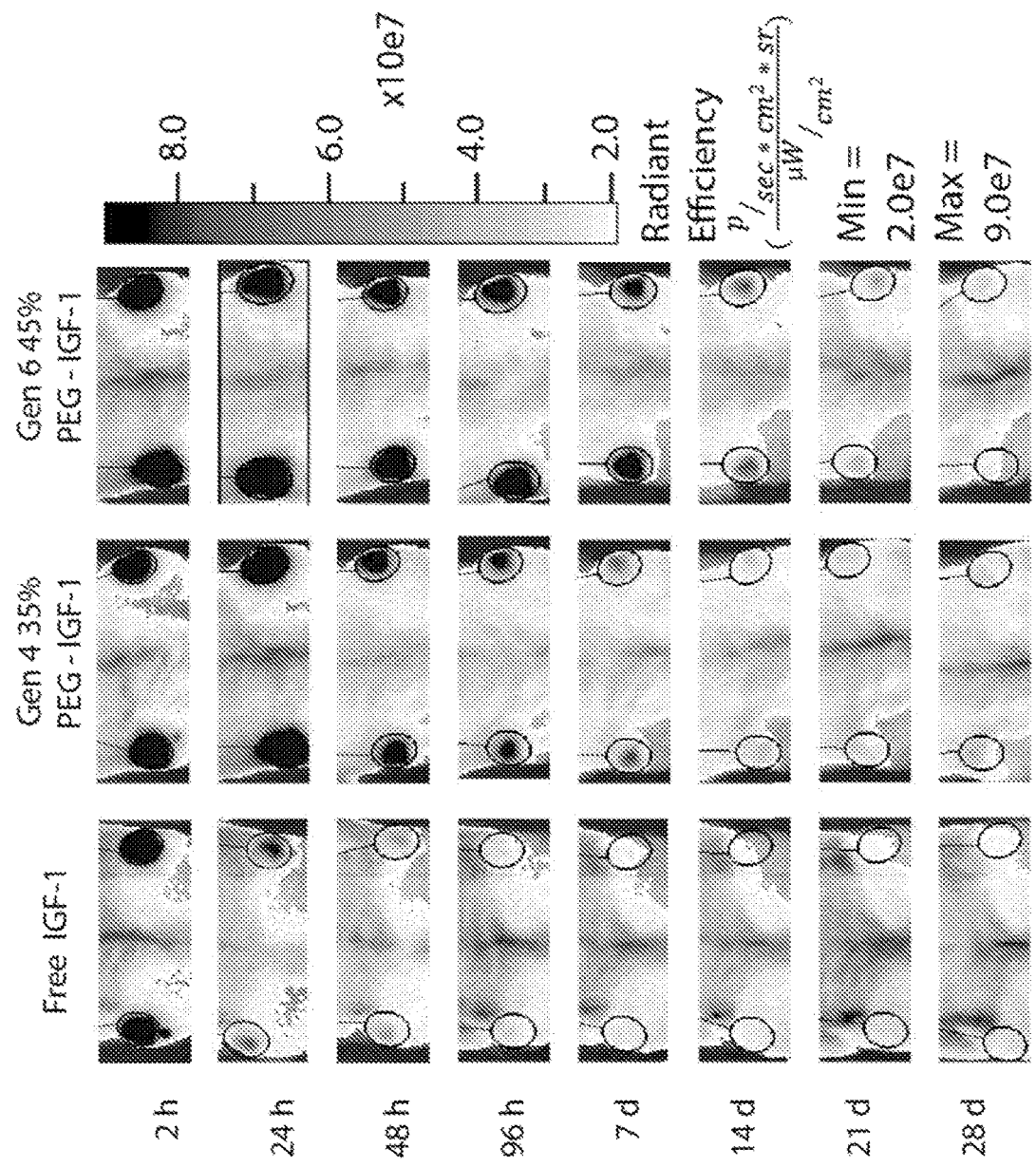

As shown in FIG. 4B, IGF-1 fluorescence was imaged in the living rats over the course of 28 days. The circled regions are the knee joints of the rats. Darker shades of grey indicate more fluorescence and more IGF-1.

Figure 4D:
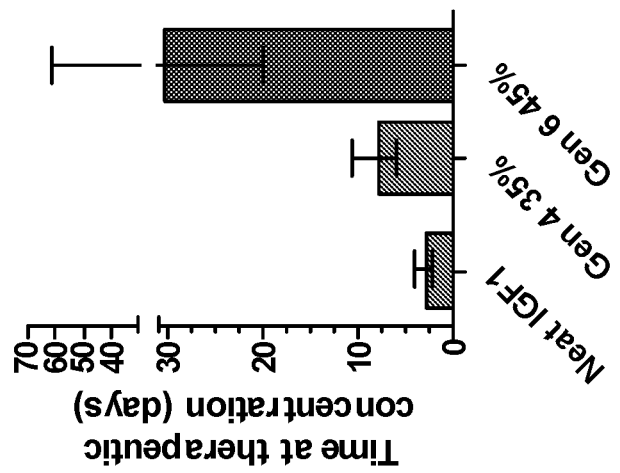
FIGS. 4C and 4D are plots derived from the data shown in FIGS. 4A and 4B indicating joint half-life and time for which API is at a therapeutically useful concentration for the conjugated dendrimers of the present invention relative to API alone.
Figure 4C:
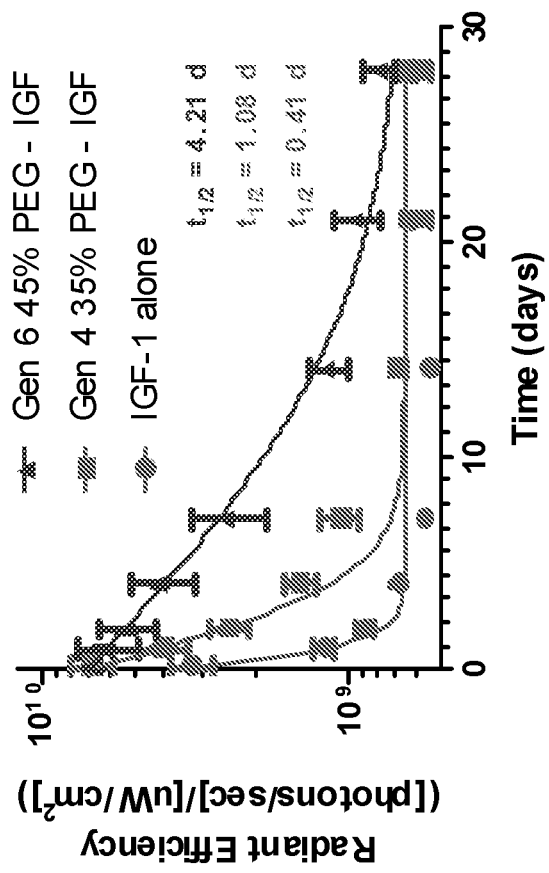

As shown in FIG. 4C, images were quantified and joint half-lives (time until half of IGF-1 in joint is cleared from the system) were calculated for each formulation. Gen 6 45% PEG-IGF-1 has 10× the half-life of IGF-1 alone.

As shown in FIG. 4D, based on doses used, Gen 6 45% PEG-IGF-1 formulation can deliver relevant doses of IGF for approximately 30 days. IGF-1 alone only remains at relevant doses for 3 days.

Half-life of the conjugated dendrimers described herein within the joint can be tailored based on adjustment of the PEGylation stoichiometry and dendrimer generation. The Gen 4 dendrimer with 35% of end-groups PEGylated achieved a joint half-life of approximately 24 hours in rats, while the Gen 6 dendrimer with 45% of end-groups PEGylated (Gen 6 45% PEG-IGF-1) achieved a joint half-life of approximately 100 hours in rats, as shown in FIGS. 4A through 4D.

Rats were sacrificed two months after injection for histological analysis of chronic organ damage. H&E stained sections of joints, liver, kidney, and lungs were found to be normal by a pathologist. Also tested was an under-PEGylated dendrimer, Gen 4 at 17% PEG (N=64, (x+y+z)/N=0.17). This dendrimer had shown mild cytotoxicity in human chondrocyte cell line. This formulation induced considerable inflammation in the synovium, indicating the importance of optimized surface charge within the window of optimal ratios as specified in this invention.

A second group of healthy rats were injected intra-articularly with Gen 6 45% PEG-IGF-1 conjugate to an approximate knee concentration of 10 μM dendrimer. Serum samples were taken from rats 2 and 7 days post-injection and levels of common toxicological biomarkers were analyzed. All biomarker levels were either within reported normal ranges or statistically equivalent to control (no injection) animals.

Example 4: Cartilage Penetration Experiments

Conjugated dendrimer described herein are capable of penetrating the thickness of human cartilage far better than the API (IGF-1) alone. The degree of penetration can be controlled by adjustment of positive surface charge, i.e. by PEGylation stoichiometry, as well as by selecting the dendrimer generation. Penetration is important to enable reaching therapeutically relevant local concentration of the API.

PEGylated Dendrimer-drug conjugates can penetrate human thickness (~1 mm) cartilage.

Figure 5A:
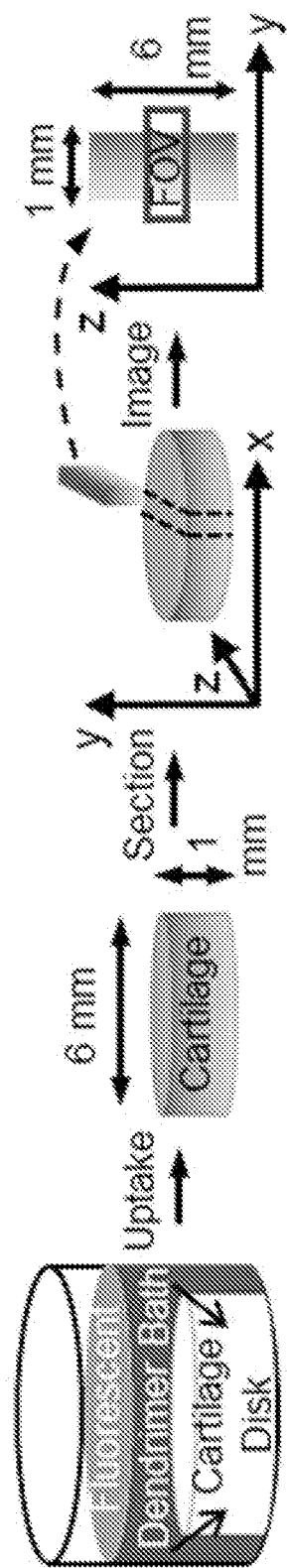
FIG. 5A illustrates experimental setup of the cartilage penetration experiments.

As shown in FIG. 5A, 6 mm bovine cartilage explants were harvested and trimmed and incubated in media as described above. They were then incubated in 750 uL of 10 uM Gen 4 35% PEG-IGF-1 or Gen 6 45% PEG-IGF-1 in DMEM, −phenol red, +10% FBS, +Pen-Strep, within a 48 well plate for 48 hours at 37° C. Explants were removed and sectioned to 6 mm×1 mm×80 μm slices with a vibrating microtome (Leica) and immediately imaged by a Nikon A1R scanning confocal microscope in bright field and Alexa 647 channels using identical settings across samples. Fluorescence intensity was quantified across the entirety of the image as a surface intensity plot.

Figure 5B:
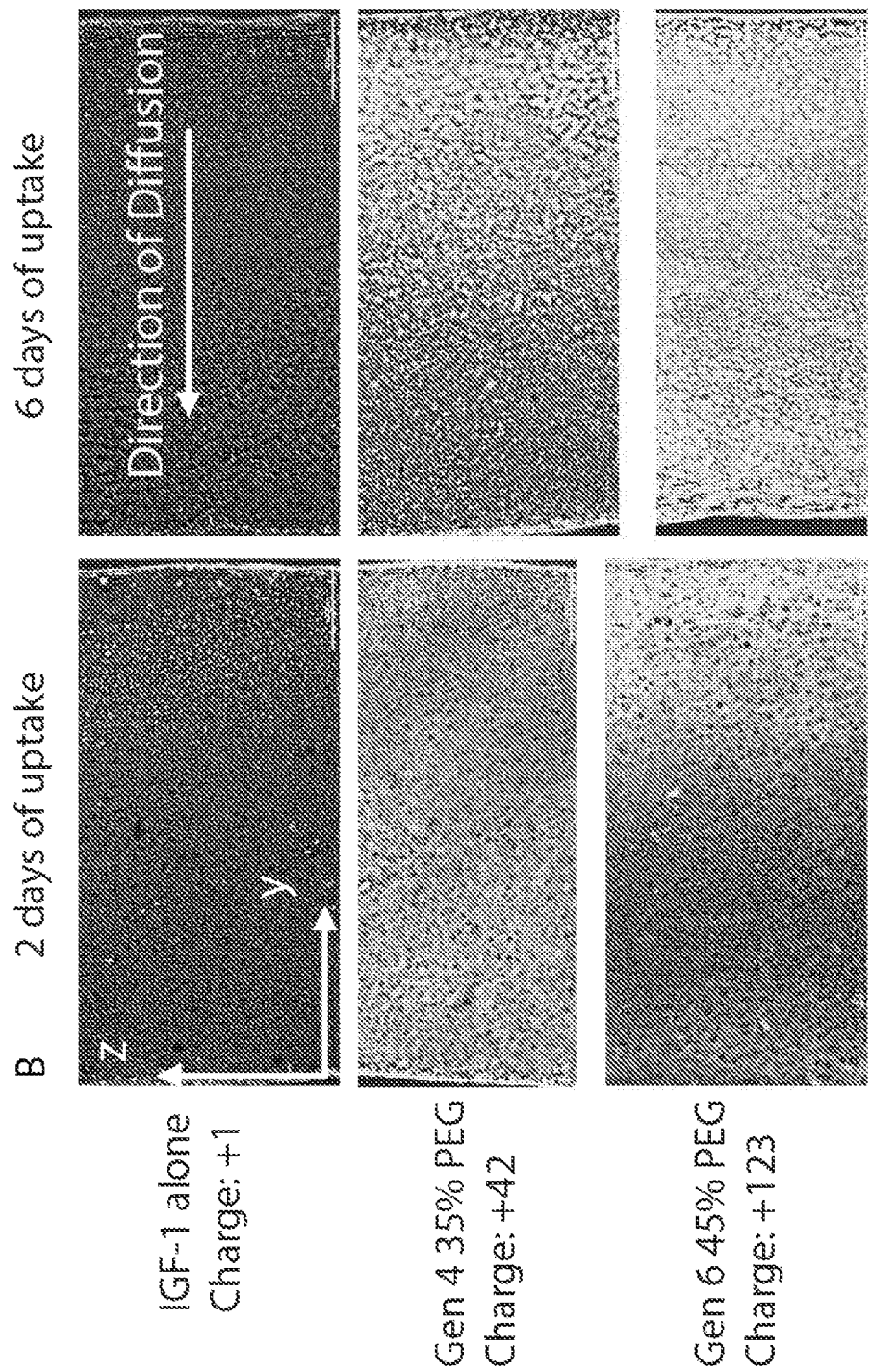
FIGS. 5B and 5C are photographs and plots, respectively, demonstrating via fluorescent intensity the penetration of the dendrimers of the present invention throughout the thickness of cartilage relative to API alone.
Figure 5C:
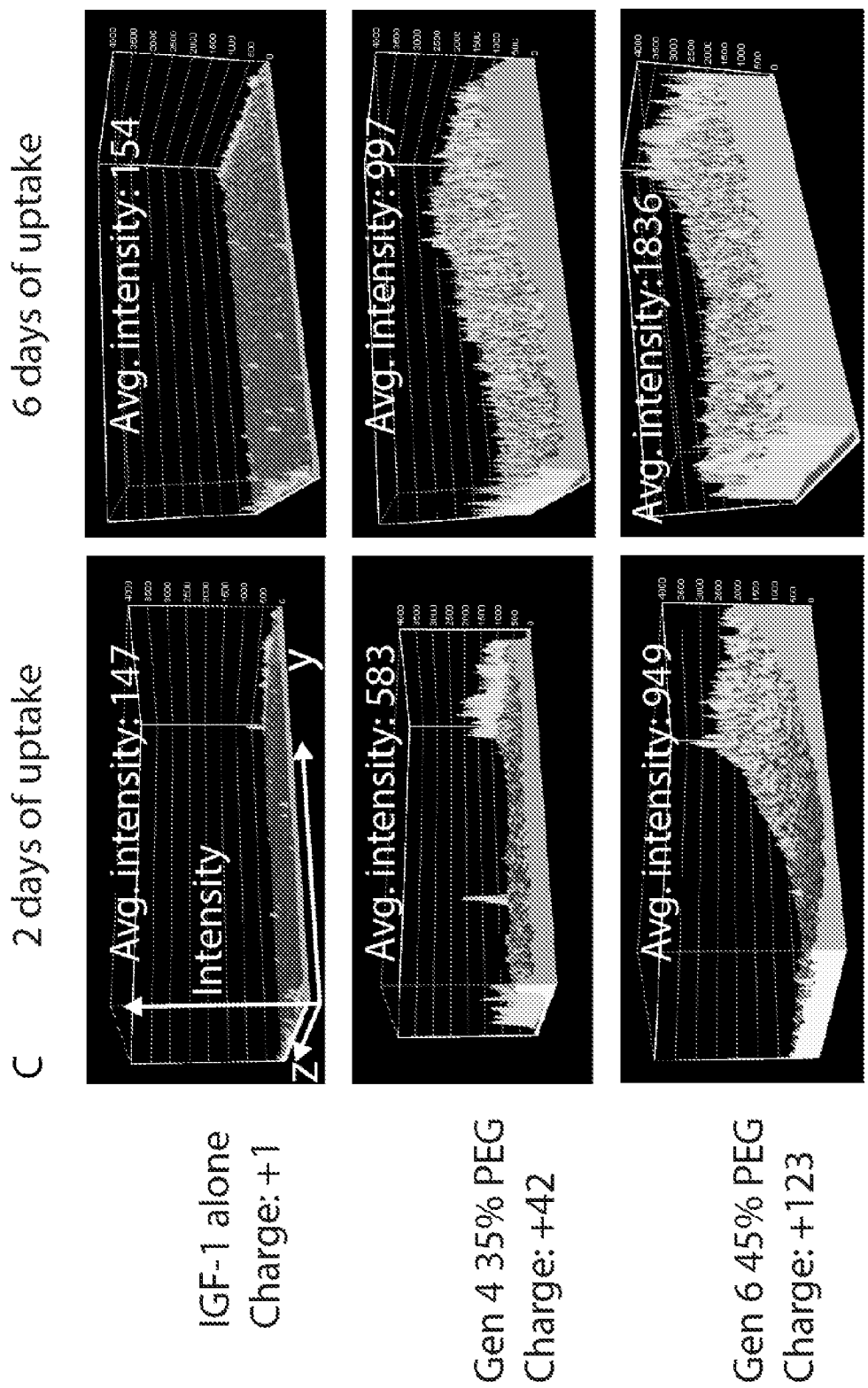

The results are presented in FIGS. 5B and 5C. (The rectangular outline in FIG. 5A is the field of view in the displayed images.)

Both PEGylated dendrimer-IGF-1 formulations had more IGF-1 bind to the tissue than IGF 1 alone, and it penetrated further into the tissue.

Fluorescent intensity is quantified across the images in FIG. 5B and presented in the graphs in FIG. 5C.

Example 5: In Vivo Histological Analysis in Rats

In this experiment, the dendrimer conjugates described herein were tested in a rat Surgical Osteoarthritis Model: ACLT+MMx.

Figure 8A:
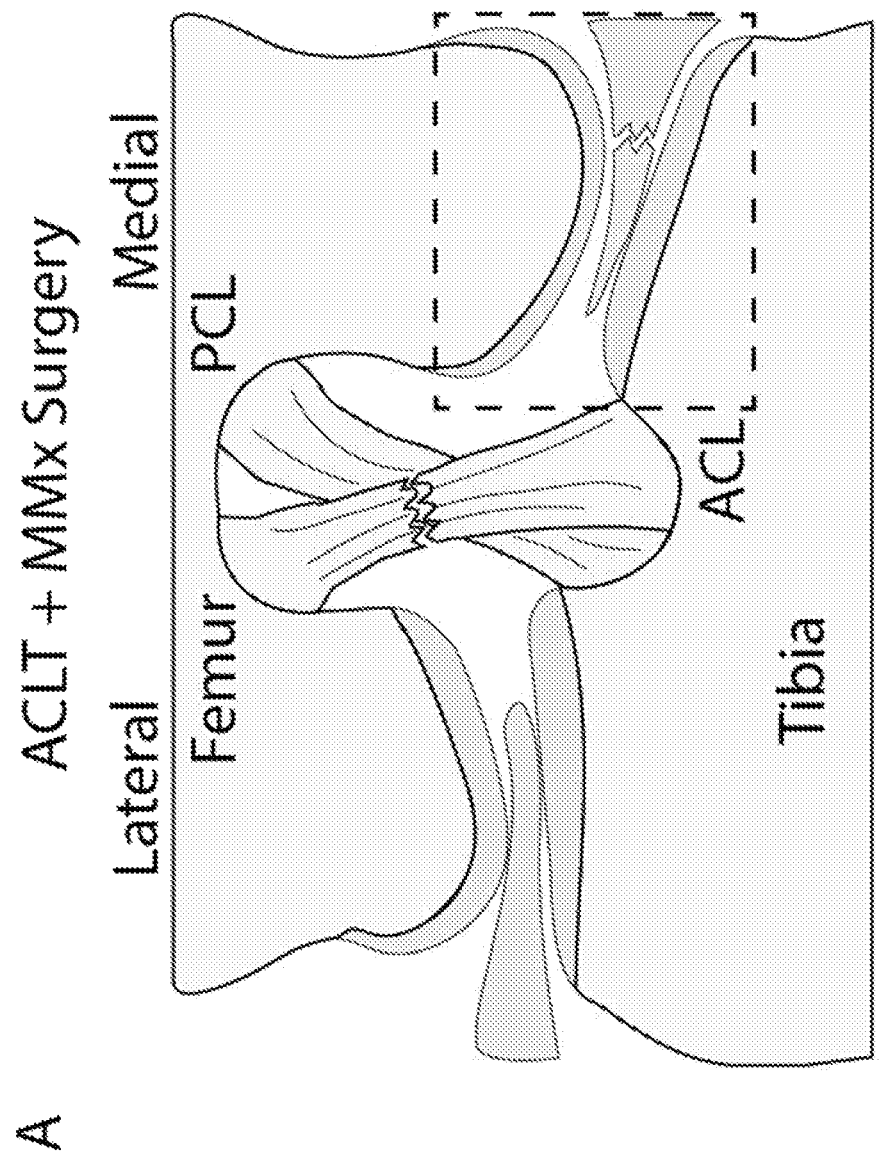
FIG. 8A is a schematic of the anterior cruciate ligament transection & partial medial meniscectomy (ACLT+MMx) surgical technique used to induce experimental osteoarthritis in rats.
Figure 8B:
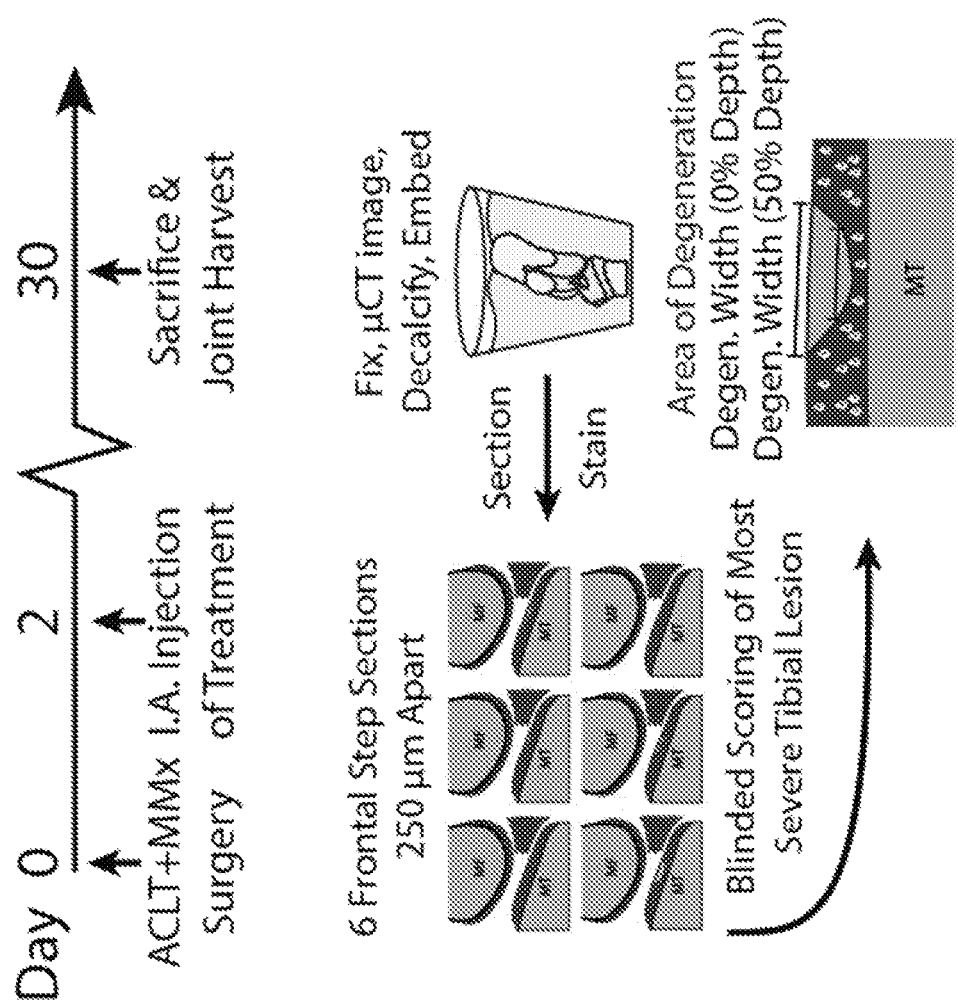
FIG. 8B is a schematic of the timeline of surgical experiments and therapeutic intervention with the present invention as well as the analytic techniques used to evaluate the therapeutic efficacy of the present invention.
Figure 8C:
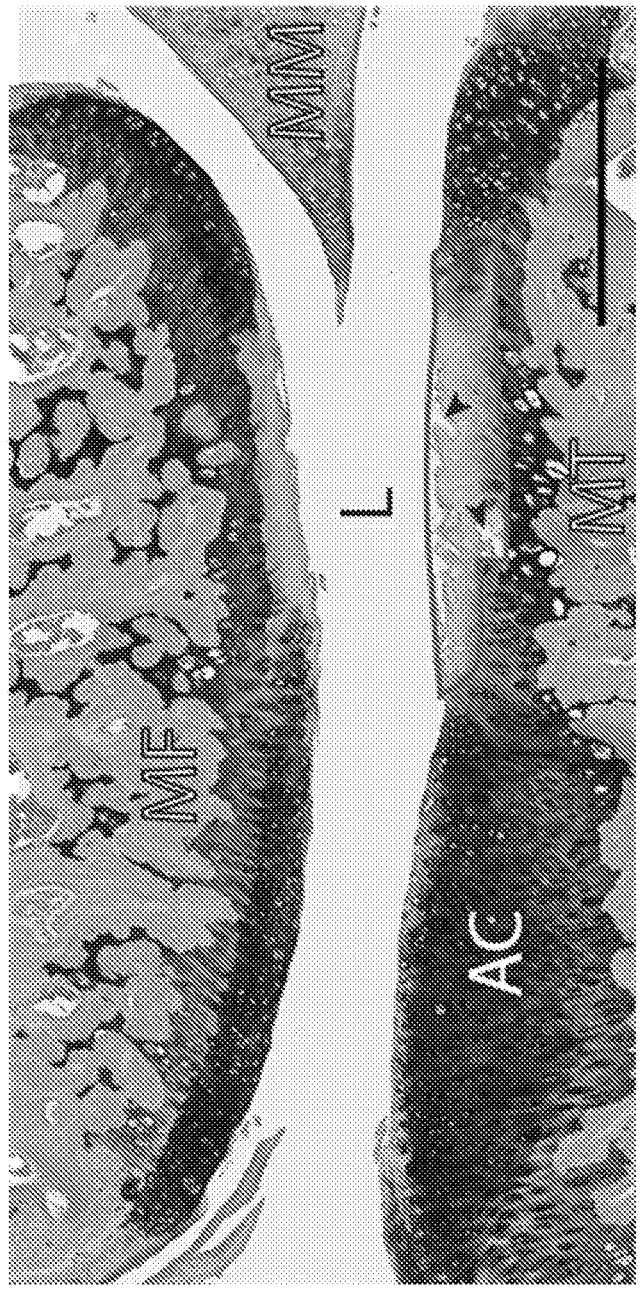
FIG. 8C is a photograph of a frontal section of a rat knee with osteoarthritis that was not treated. Area of degeneration is outlined. Scale is 500 µm.
Figure 8D:
FIG. 8D is a photograph of a frontal section of a rat knee with osteoarthritis that was treated with unmodified API. Width of degeneration in the frontal section at 0% and 50% tissue depth are outlined. Scale is 500 µm.
Figure 8E:
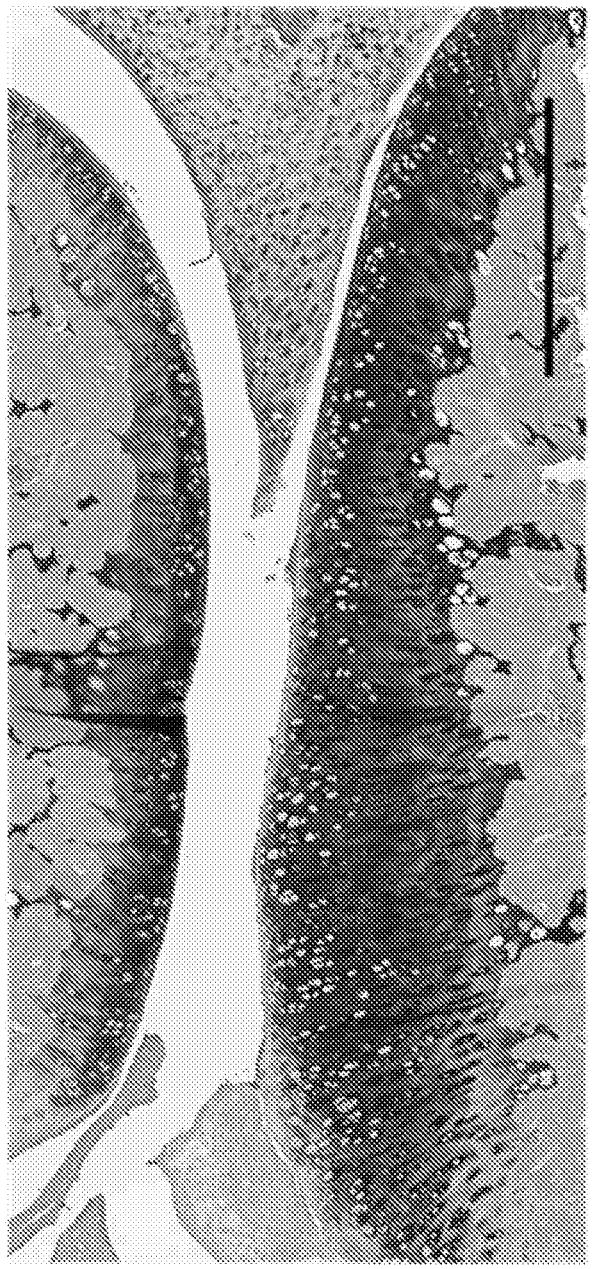
FIG. 8E is a photograph of a frontal section of a rat knee with osteoarthritis that was treated with dendrimer-API conjugate of the present invention, specified as Gen 6 45% PEG-IGF-1. Scale is 500 µm.
Figure 8F:
FIG. 8F is a photograph of a frontal section of a rat knee that received only sham surgery and has not developed osteoarthritis. Scale is 500 µm.

Skeletally mature male Sprague-Dawley rats of 12 weeks of age (350-400 g, Taconic) were injured by the Anterior Cruciate Ligament Transection and Partial Medial Meniscectomy (ACLT+pMMx) method to induce arthritis. FIG. 8A is a schematic diagram of the performed surgery. Rats were divided into 4 groups: Transection and no treatment (untreated), Transection and free IGF-1 treatment (free IGF-1), Transection and Gen 6 45% PEG-IGF-1 treatment (Gen 6 45%—IGF-1), and sham surgery (Sham). FIG. 8B is a schematic diagram of the experimental timeline and process used to generate histological and micro-computed tomography (μCT) data from the experiment. Treatments were given by intra-articular injection into the affected joint 48 hours after surgery, using a joint concentration of 6 M IGF-1. Rats were sacrificed for analysis 30 days after surgery.

Histological Processing and Analysis

Histological processing and analysis was performed according to the guidelines for rat surgical models by the Osteoarthritis Research Society International (OARSI) histopathology initiative (Gerwin et al, Osteoarthritis and Cartilage, 2010, Schmitz et al, Osteoarthritis and Cartilage 2010). See FIG. 8B. Six 250 μm frontal step sections were taken from the central ~1.5 mm of the joint and stained with Toluidine Blue/Fast Green. Aggrecan in healthy cartilage is stained blue (dark) and collagens in bone or degenerated cartilage are stained green (light). The section with the most severe medial tibia cartilage lesion was identified by a blinded investigator and used for all further analysis. Sections were scored quantitatively for degeneration in a blinded manner by histomorphometry techniques based on OARSI histopathology initiative guidelines.

Results are presented in FIGS. 8C through 8F. Representative toluidine blue/fast green stained frontal sections of the medial femur and tibia. Area of degeneration is outlined. Total and significant widths of degeneration are outlined at 0% depth and 50% depth, respectively. Matrix loss shown as arrows. MF: medial femur, MT: medial tibia, MM: medial meniscus, AC: articular cartilage, L: Lesion. Scale: 500 μm.

Figure 8G:
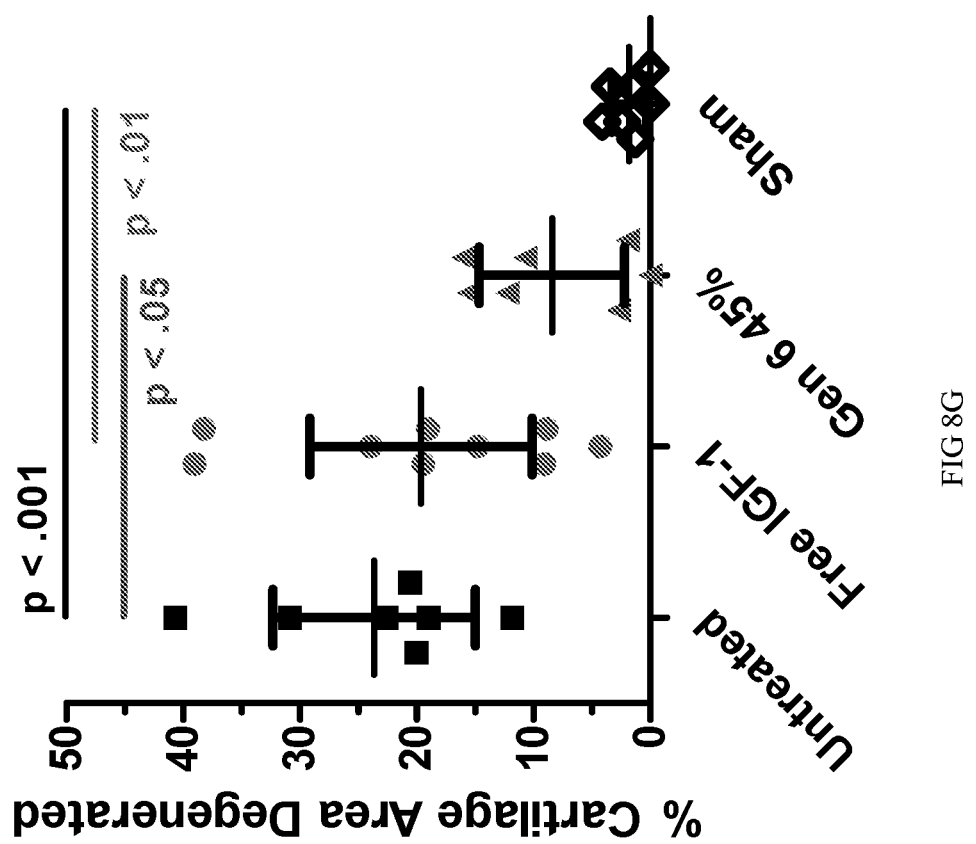
FIG. 8G is a scatterplot of the data derived from images shown in FIG. 8C-F showing area of degenerated tissue across all rats studied.
Figure 8H:
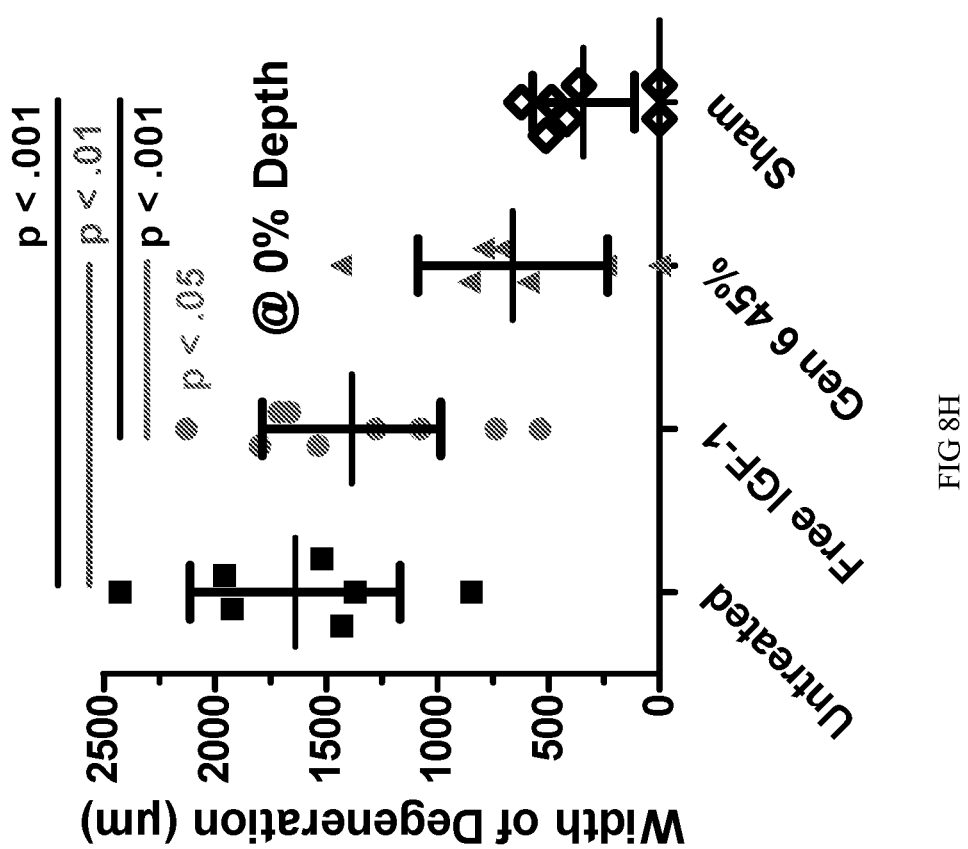
FIG. 8H is a scatterplot of the data derived from images shown in FIG. 8C-F showing width of degeneration at 0% depth in the tissue.
Figure 8I:
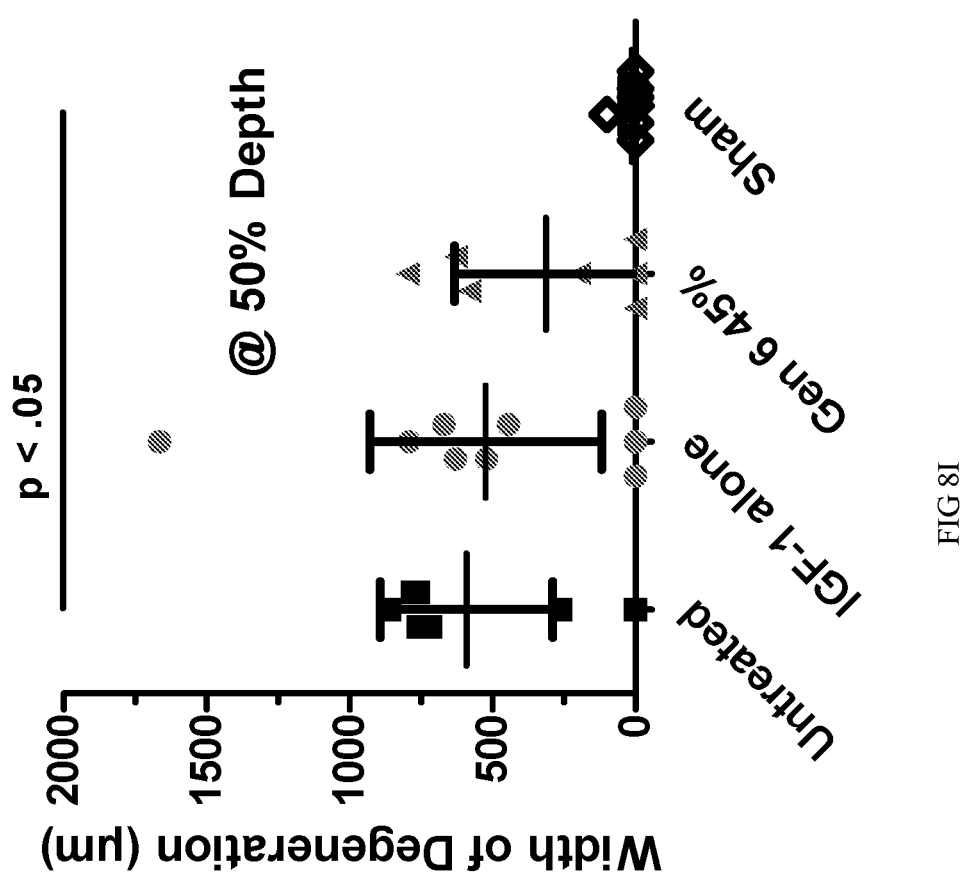
FIG. 8I is a scatterplot of the data derived from images shown in FIG. 8C-F showing width of degeneration at 50% depth in the tissue.

Quantitative analysis of the results shown in FIGS. 8C through 8F are presented in FIGS. 8G-8I. FIG. 8G shows quantified area of degenerated cartilage tissue of the medial tibia for each rat, as a % of total cartilage area in the section. Degenerated tissue was defined as >50% cell death and loss of toluidine blue staining. FIG. 8H shows width of cartilage degeneration at the joint surface (0% depth). FIG. 8I shows width of cartilage degeneration at 50% cartilage depth. Data are means+95% CIs, N=7-9 as shown, statistics by one-way ANOVA and Tukey HSD post-test.

Rats treated with Gen 6 45% PEG-IGF-1 (D=PAMAM, Generation=6, N=256, Ratio (x+y+z)/N=0.45, CSG=PEG$_8$, MW=435 Da, API=IGF-1) after surgery showed mean degeneration of only 8.4% of medial tibial cartilage area [(FIG. 8G)]. This was significantly less (p=0.017) than the untreated group, with a mean area degeneration of 23.7%. Free IGF-1 reduced area degeneration to 19.7%, but this was not significant. Similar trends were seen for widths of degeneration (FIG. 8H). At the cartilage surface (0% tissue depth), the mean width of degenerated tissue among rats treated with Gen 6 45% PEG$_8$-IGF-1 was 661 μm, compared to 1390 μm for IGF-1 alone and 1640 μm for no treatment. Surface degeneration following Gen 6 45% PEG-IGF-1 was statistically less than both groups (p=0.0023 vs untreated, p=0.020 vs free IGF-1) and statistically equivalent (p=0.57) to the sham operation, with a mean surface degeneration of only 343 μm.

These data show that the main embodiment of this invention, Gen 6 45% PEG$_8$-IGF-1), provides a significant improvement in the condition of rats with osteoarthritis using a well-established animal model. In contrast, the API (free IGF-1) alone does not provide a meaningful improvement in the rats. The drug delivery provided by this invention makes the API much more effective.

Example 6: Micro-Computed Tomography Scan of Rat Joints

After fixation and before decalcification, excised rat joints were attached to the bore of a microCT scanner (GE eXplore CT 120) and scanned at 0.03° angles for a total of 1200 scans over a time period of 1.5 hours. Scans used an 80 kV x-ray potential, 32 mA current, and a 100 ms integration time. Image data sets were reconstructed into regions of interest encompassing single joints using Microview software (Parallax Innovations).

3D positioning data were used to quantify total volume of osteophytes (bone spurs) on each joint. 3D DICOM analysis software (Osirix MD) was used by a blinded investigator to re-section the images into a uniform frontal plane, perpendicular to an axis tangential to the femoral condyles and tibial plateau in the sagittal plane and an axis bisecting the femoral condyles and tibial plateau in the transverse plane. Osteophytes were identified and traced serially in 2D frontal sections in a blinded manner following the methods of Batiste et al., Osteoarthritis & Cartilage, 2004, based on protrusion from the normal bone contour and reduced bone mineral density. The sections were then reconstructed to 3D, and total osteophyte ROI volume was calculated for each rat.

Figure 9:
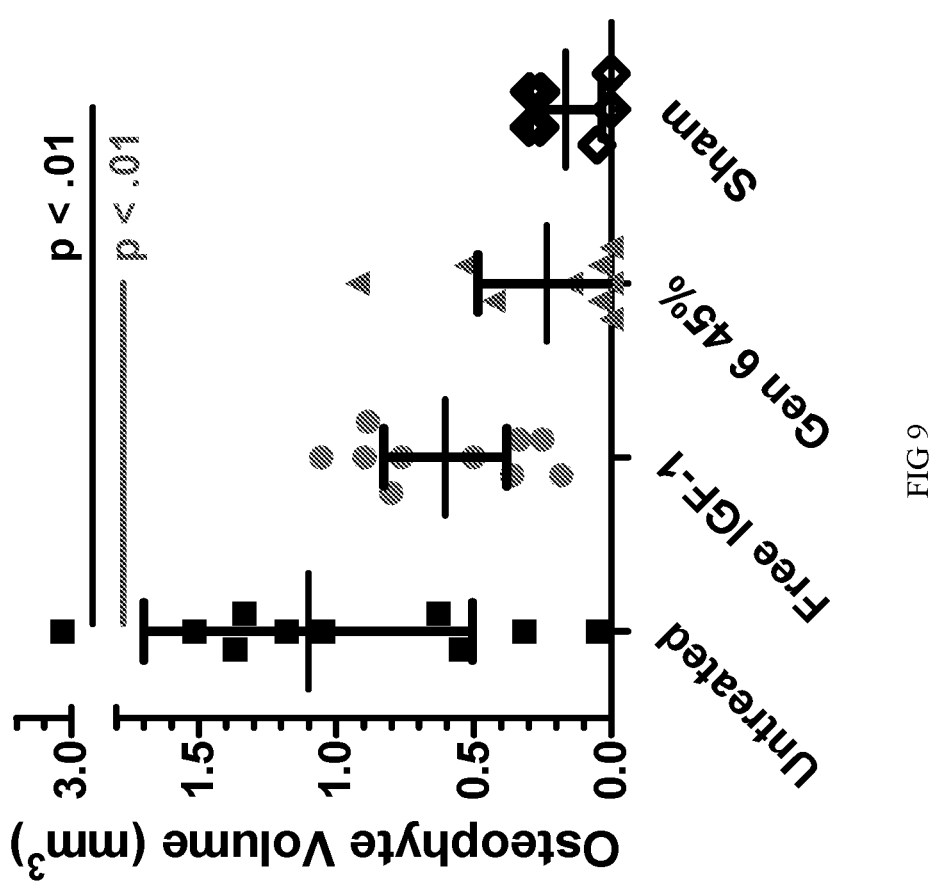
FIG. 9 is a scatterplot of total osteophyte volume as determined by micro-computed tomography imaging of the operated joint of all rats studied.

Results are presented in FIG. 9. ROIs were serially drawn around osteophytes in sequential frontal image stacks and reconstructed into 3D to generate bottom images and measure osteophyte volume. Total osteophyte volume in each joint across the four treatment conditions is shown in FIG. 9. Data are means+95% CI, N=7-9 as shown, statistics by one way ANOVA and Tukey HSD post-test.

A single injection of free IGF-1 following surgery substantially reduced osteophyte burden by nearly 50% (1.10 to 0.60 mm$^3$) but this effect was not statistically significant (p=0.14). A single injection of Gen 6 45% dendrimer IGF-1 was even more effective, resulting in a mean total osteophyte burden of 0.23 mm$^3$, which constituted a statistically significant reduction (p=0.004) from untreated rats and was nearly equivalent to osteophyte burden of sham operated rats (0.17 mm$^3$, p=0.99).

These data show the improvement in osteoarthritic rats in response to API conjugated to the dendrimers of the present invention.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:
1. A conjugated dendrimer, represented by the following structural formula:

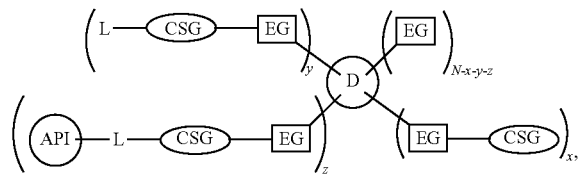

or a pharmaceutically acceptable salt thereof
wherein:
D is a cationic dendrimer having end groups EG, wherein each EG includes an amine moiety,
each L is a linker;
each API is an active pharmaceutical ingredient;
N is an integer power of 2 from 64 to 256;
x, y, and z, each independently, is an integer from 1 to N; and
wherein:
(i) each CSG is a charge-shielding group having molecular weight of equal to or greater than 200 and less than 400 Da; and
the ratio of (x+y+z)/N is from about 0.6 to about 0.9 or from about 0.4 to about 0.8;
(ii) each CSG is a charge-shielding group having molecular weight of equal to or greater than 400 and less than 614 Da; and
the ratio of (x+y+z)/N is from about 0.2 to about 0.6;
(iii) each CSG is a charge-shielding group having molecular weight of equal to or greater than 614 and less than 820 Da; and
the ratio of (x+y+z)/N is from about 0.15 to about 0.50; or
(iv) each CSG is a charge-shielding group having molecular weight of equal to or greater than 820 and less than or equal to 1085 Da; and
the ratio of (x+y+z)/N is from about 0.1 to about 0.4.
2. The conjugated dendrimer of claim 1, wherein:
each CSG is a charge-shielding group having molecular weight of equal to or greater than 200 and less than 400 Da;
N is 64; and
the ratio of (x+y+z)/N is from about 0.6 to about 0.9.
3. The conjugated dendrimer of claim 1, wherein:
each charge-shielding group CSG is a PEG having from 8 to 12 units;
N is 64; and
the ratio of (x+y+z)/N is from about 0.2 to about 0.6.
4. The conjugated dendrimer of claim 1, wherein:
each charge-shielding group CSG is a PEG having from 8 to 12 units;
the dendrimer D is a polyamidoamine (PAMAM) dendrimer of Generation 4; and
the ratio of (x+y+z/N) is from about 0.3 to about 0.45.

5. The conjugated dendrimer of claim 1, wherein:
each CSG is a charge-shielding group having molecular weight of equal to or greater than 400 and less than 614 Da;
N is 64; and
the ratio of (x+y+z)/N is from about 0.2 to about 0.6.
6. The conjugated dendrimer of claim 1, wherein:
each CSG is a charge-shielding group having molecular weight of equal to or greater than 614 and less than 820 Da;
N is 64; and
the ratio of (x+y+z)/N is from about 0.15 to about 0.50.
7. The conjugated dendrimer of claim 1, wherein:
each CSG is a charge-shielding group having molecular weight of equal to or greater than 820 and less than or equal to 1085 Da;
N is 64; and
the ratio of (x+y+z)/N is from about 0.1 to about 0.4.
8. The conjugated dendrimer of claim 1, wherein:
each CSG is a charge-shielding group having molecular weight of equal to or greater than 200 and less than 400 Da;
N is 256; and
the ratio of (x+y+z)/N is from about 0.4 to about 0.8.
9. The conjugated dendrimer of claim 1, wherein:
each charge-shielding group CSG is a PEG having from 8 to 12 units;
N is 256; and
the ratio of (x+y+z)/N is from about 0.2 to about 0.6.
10. The conjugated dendrimer of claim 1, wherein:
each charge-shielding group CSG is a PEG having from 8 to 12 units;
the dendrimer D is a polyamidoamine (PAMAM) dendrimer of Generation 6; and
the ratio of (x+y+z/N) is from about 0.4 to about 0.5.
11. The conjugated dendrimer of claim 1, wherein:
each CSG is a charge-shielding group having molecular weight of equal to or greater than 400 and less than 614 Da;
N is 256; and
the ratio of (x+y+z)/N is from about 0.2 to about 0.6.
12. The conjugated dendrimer of claim 1, wherein:
each CSG is a charge-shielding group having molecular weight of equal to or greater than 614 and less than 820 Da;
N is 256; and
the ratio of (x+y+z)/N is from about 0.15 to about 0.5.
13. The conjugated dendrimer of claim 1, wherein:
each CSG is a charge-shielding group having molecular weight of equal to or greater than 825 and less than or equal to 1085 Da;
N is 256; and
the ratio of (x+y+z)/N is from about 0.15 to about 0.4.
14. The conjugated dendrimer of claim 1, wherein the cationic dendrimer includes at least one repeat units represented by the following structural formulas:

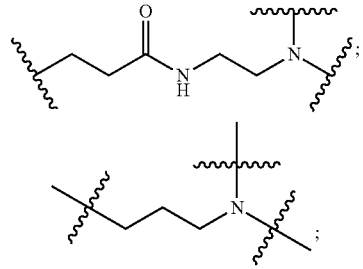

-continued

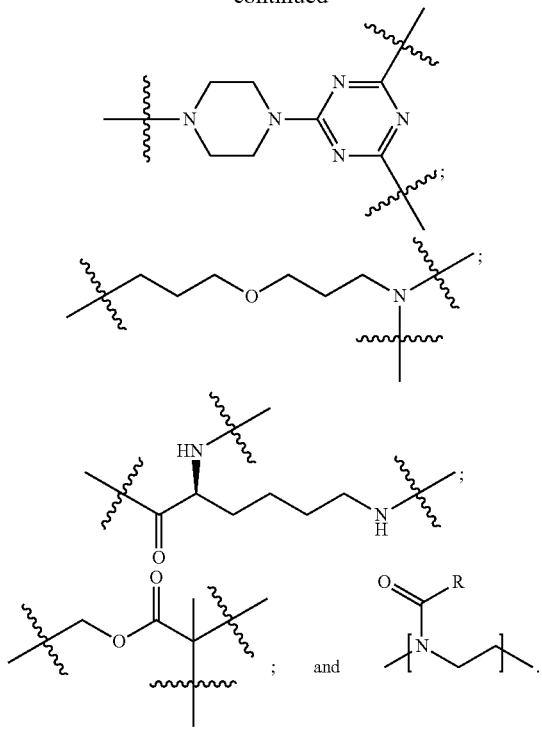

15. The conjugated dendrimer of claim 1, wherein the charge-shielding group is selected from a polyethylene glycol (PEG), a poly(2-oxazoline), a polybetaine, a polyacrylate, a polyacrylamide, an amino acid; a peptide; a fatty acid or phospholipid, an oligosaccharide; a glycosaminoglycan; a polyanhydride, a polyglycidol; a polyacetal; a polyglycerol, and a polyphosphoester.

16. The conjugated dendrimer of claim 1, wherein the charge-shielding group is a polyethylene glycol (PEG).

17. The conjugated dendrimer of claim 1, wherein the linker is represented by any one of the following structural formulas:

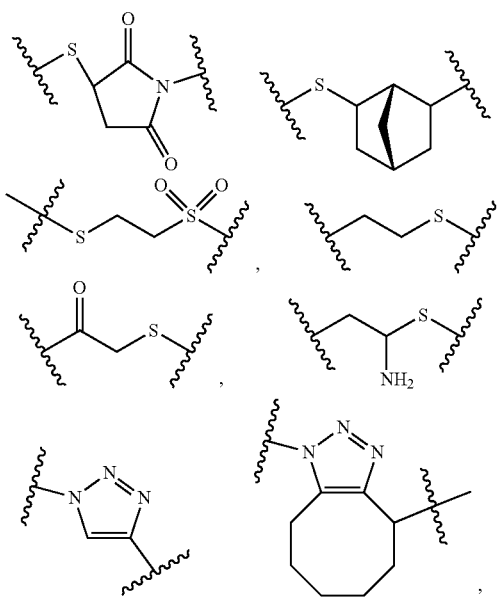

-continued

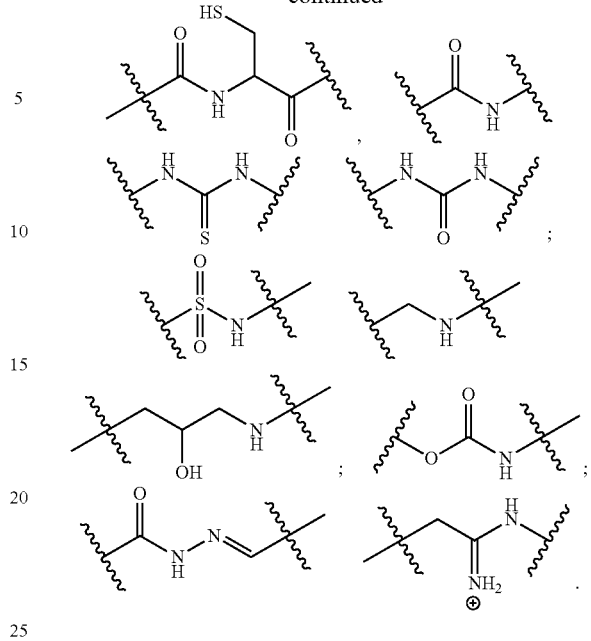

18. The conjugated dendrimer of claim 1, wherein the linker includes a moiety represented by any one of the following structural formulas:

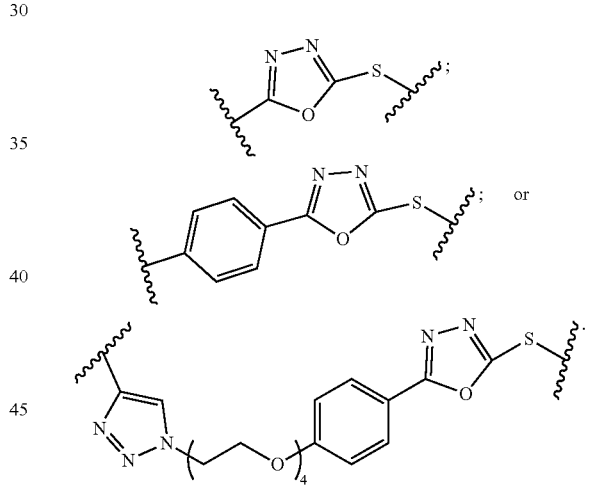

19. The conjugated dendrimer of claim 1, wherein the linker include a peptide substrate of any one or more of the following enzymes: matrix metalloprotease 13 (MMP13); Cathepsin B; Cathepsin K; ADAMTS-4; and ADAMTS-5.

20. The conjugated dendrimer of claim 1, wherein the API is selected from a biologically active polypeptide, a monoclonal antibody, a nonsteroidal anti-inflammatory drug (NSAIDS), a matrix metallopeptidase inhibitor, a cytokine inhibitor, and a nucleic acid.

21. The conjugated dendrimer of claim 1, wherein the API is selected from Insulin-like Growth Factor 1 (IGF-1), a Fibroblast Growth Factor 18 (FGF-18), dexamethasone, a matrix metallopeptidase MMP13 inhibitor, an IL1 receptor antagonist, a TGFB inhibitor, a TNFalpha inhibitor, and kartogenin.

22. The conjugated dendrimer of claim 1, wherein the cationic dendrimer D is a PAMAM, and each end-group EG is —NH$_2$.

23. The conjugated dendrimer of claim 1, wherein each linker L includes a thiol-maleimide moiety represented by the following structural formula:

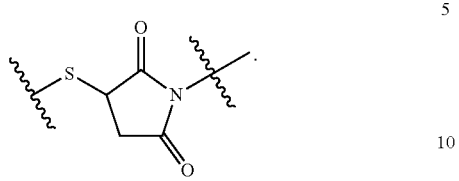

24. The conjugated dendrimer of claim 1, wherein the API is a biologically active polypeptide.

25. The conjugated dendrimer of claim 1, wherein the cationic dendrimer is a G4 PAMAM, wherein each end-group is —$NH_2$ and N is 64 or a G6 PAMAM, wherein each end-group is —$NH_2$ and N is 256.

26. The conjugated dendrimer of claim 25, wherein each linker L is a thiol-maleimide moiety represented by the following structural formula:

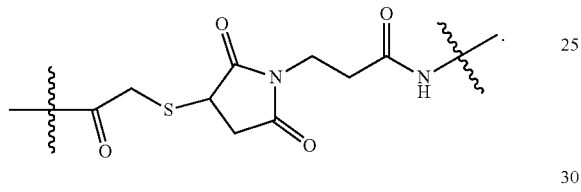

27. The conjugated dendrimer of claim 26, wherein each API is a human IGF-1.

28. The conjugated dendrimer of claim 1, wherein the conjugated dendrimer is represented by the following structural formula:

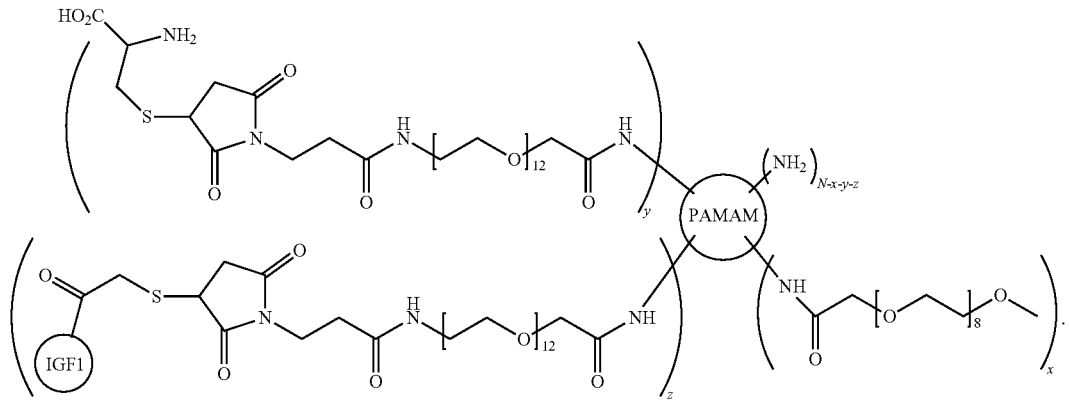

29. A pharmaceutical composition, comprising a conjugated dendrimer of claim 1 in a pharmaceutically acceptable carrier.

30. A method of treating a disorder of an articular joint cartilage, comprising:
administering by an intra-articulate injection to a subject in need thereof a therapeutically effective amount of a conjugated dendrimer of claim 1,
wherein the disorder is an articular joint arthritis or an articular joint cartilage injury.

* * * * *